United States Patent
Scott et al.

(10) Patent No.: US 9,796,990 B2
(45) Date of Patent: Oct. 24, 2017

(54) ENZYMES FOR DEGRADING ORGANOPHOSPHATES

(75) Inventors: Colin Scott, Melba (AU); John Oakeshott, Wanniassa (AU); Robyn Russell, Wanniassa (AU); Nigel French, Kambah (AU); Steven Kotsonis, Brunswick (AU); Kaiyan Liu, Bundoora (AU)

(73) Assignee: COMMONWEALTH SCIENTIFIC AND INDUSTRIAL RESEARCH ORGANIZATION, Campbell (AU)

( * ) Notice: Subject to any disclaimer, the term of this patent is extended or adjusted under 35 U.S.C. 154(b) by 0 days.

(21) Appl. No.: 14/233,878

(22) PCT Filed: Jul. 20, 2012

(86) PCT No.: PCT/AU2012/000869
§ 371 (c)(1),
(2), (4) Date: Jul. 24, 2014

(87) PCT Pub. No.: WO2013/010225
PCT Pub. Date: Jan. 24, 2013

(65) Prior Publication Data
US 2014/0342387 A1  Nov. 20, 2014

Related U.S. Application Data

(60) Provisional application No. 61/510,337, filed on Jul. 21, 2011, provisional application No. 61/509,810, filed on Jul. 20, 2011.

(51) Int. Cl.

| | |
|---|---|
| *C12N 9/16* | (2006.01) |
| *C12P 9/00* | (2006.01) |
| *C12Q 1/44* | (2006.01) |
| *C12Q 1/00* | (2006.01) |
| *C12Q 1/42* | (2006.01) |
| *A62D 3/02* | (2007.01) |
| *A61K 38/00* | (2006.01) |
| *A62D 101/04* | (2007.01) |
| *A62D 101/26* | (2007.01) |

(52) U.S. Cl.
CPC .......... *C12P 9/00* (2013.01); *A62D 3/02* (2013.01); *C12N 9/16* (2013.01); *C12Q 1/005* (2013.01); *C12Q 1/42* (2013.01); *C12Q 1/44* (2013.01); *C12Y 301/08001* (2013.01); *C12Y 301/08002* (2013.01); *A61K 38/00* (2013.01); *A62D 2101/04* (2013.01); *A62D 2101/26* (2013.01); *C07K 2319/00* (2013.01); *C07K 2319/036* (2013.01); *G01N 2430/10* (2013.01)

(58) Field of Classification Search
CPC .... C12Y 301/08001; C12N 9/16; C12Q 1/44; C12P 9/00
USPC .......... 435/196, 195, 19, 131, 252.1, 320.1
See application file for complete search history.

(56) References Cited

U.S. PATENT DOCUMENTS

| | | |
|---|---|---|
| 4,945,050 A | 7/1990 | Sanford et al. |
| 5,004,863 A | 4/1991 | Umbeck |
| 5,104,310 A | 4/1992 | Saltin |
| 5,141,131 A | 8/1992 | Miller et al. |
| 5,159,135 A | 10/1992 | Umbeck et al. |
| 5,177,010 A | 1/1993 | Goldman et al. |
| 5,362,865 A | 11/1994 | Austin |
| 5,384,253 A | 1/1995 | Krzyzek et al. |
| 5,416,011 A | 5/1995 | Hinchee et al. |
| 5,463,174 A | 10/1995 | Moloney et al. |
| 5,472,869 A | 12/1995 | Krzyzek et al. |
| 5,484,728 A | 1/1996 | Serdar et al. |
| 5,518,908 A | 5/1996 | Corbin et al. |
| 5,569,834 A | 10/1996 | Hinchee et al. |
| 5,589,386 A | 12/1996 | Serdar |
| 5,589,617 A | 12/1996 | Nehra et al. |
| 5,756,671 A | 5/1998 | Gyuris et al. |
| 5,792,294 A | 8/1998 | Randazzo et al. |
| 5,859,347 A | 1/1999 | Brown et al. |
| 6,100,447 A | 8/2000 | Wu et al. |
| 6,469,145 B1 | 10/2002 | Rastogi et al. |
| 6,498,235 B2 | 12/2002 | Sheppard et al. |
| 6,541,257 B2 | 4/2003 | Lemaux et al. |
| 6,943,234 B2 | 9/2005 | Raymond et al. |
| 7,396,980 B2 | 7/2008 | Simmons et al. |
| 7,485,715 B2 | 2/2009 | Alexandrov et al. |

(Continued)

FOREIGN PATENT DOCUMENTS

| | | |
|---|---|---|
| AU | 667939 | 4/1996 |
| CA | 2092588 | 9/1994 |

(Continued)

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Bowie et al., (1990) "Deciphering the message in protein sequences: tolerance to amino acid substitutions" Science 257:1306-1310.
Greenspan et al., (1999) "Defining epitopes: It's not as easy as it seems" Nature Biotechnology 7:936-937.
Dec. 22, 2006 Office Action, issued in connection with U.S. Appl. No. 10/477,469.
Mar. 6, 2007 Response to Office Action, filed in connection with U.S. Appl. No. 10/477,469.

(Continued)

*Primary Examiner* — Robert Mondesi
*Assistant Examiner* — Md. Younus Meah
(74) *Attorney, Agent, or Firm* — John P. White; Cooper & Dunham LLP

(57) ABSTRACT

The present invention relates to enzymes capable of hydrolysing organophosphate (OP) molecules. In particular, the invention relates to variants of the OpdA enzyme from *Agrobacterium* that display improved activity when compared to the naturally occurring OpdA. The invention is also towards polypeptides that have organophosphate hydrolysing activity for the organophosphates chlorpyrifos methyl, diazinon and parathion ethyl.

14 Claims, 4 Drawing Sheets

(56) References Cited

U.S. PATENT DOCUMENTS

Figure 1:
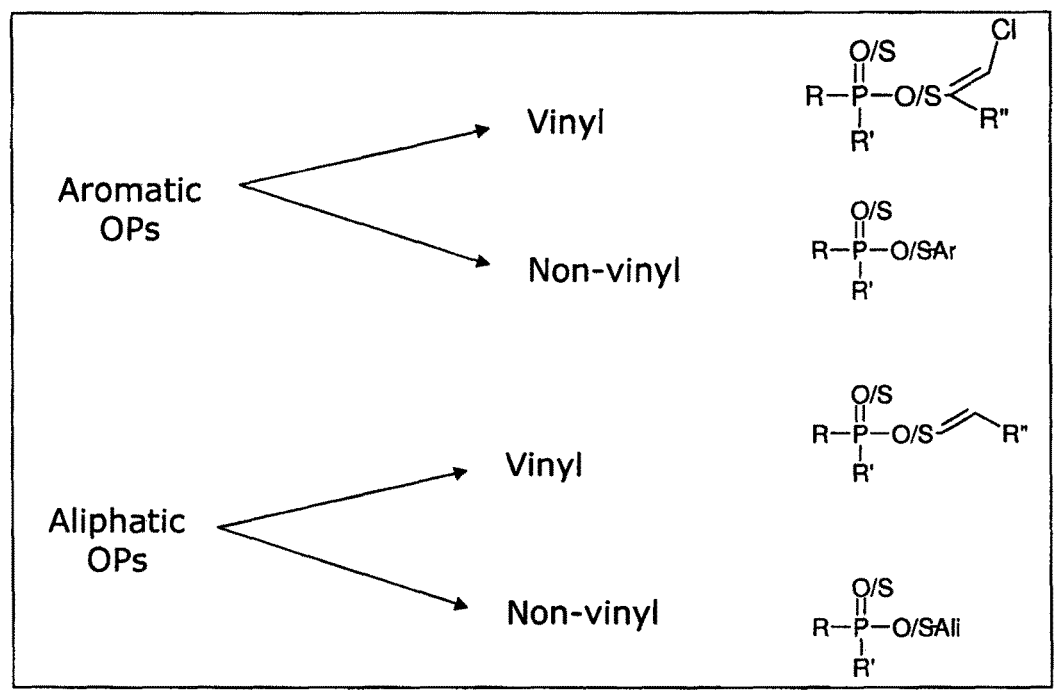

| | | | |
|---|---|---|---|
| 7,638,602 | B2 | 12/2009 | Presnell et al. |
| 8,293,244 | B2 | 10/2012 | Horne et al. |
| 8,557,547 | B2 | 10/2013 | Horne et al. |
| 2004/0161818 | A1* | 8/2004 | Horne .................. C12N 9/16 435/69.1 |

FOREIGN PATENT DOCUMENTS

| | | |
|---|---|---|
| WO | WO 84/02913 | 8/1984 |
| WO | WO 87/06614 | 11/1987 |
| WO | WO 90/02177 | 3/1990 |
| WO | WO 92/09696 | 6/1992 |
| WO | WO 93/21335 | 10/1993 |
| WO | WO 94/19930 | 9/1994 |
| WO | WO 95/19440 | 7/1995 |
| WO | WO 95/19440 A1 | 7/1995 |
| WO | WO 97/19176 A1 | 5/1997 |
| WO | WO 97/48814 | 12/1997 |
| WO | WO 99/14314 | 3/1999 |
| WO | WO 99/53037 A2 | 10/1999 |
| WO | WO 00/64539 | 11/2000 |
| WO | WO 00/65081 | 11/2000 |
| WO | WO 02/092803 A1 | 11/2002 |
| WO | WO 2004/112482 A2 | 12/2004 |
| WO | WO 2005/026269 A1 | 3/2005 |
| WO | WO 2005/059125 A1 | 6/2005 |
| WO | WO 2009/082525 A2 | 7/2009 |

OTHER PUBLICATIONS

May 17, 2007 Office Action, issued in connection with U.S. Appl. No. 10/477,469.

Oct. 17, 2007 Response'To Office Action, filed in connection with U.S. Appl. No. 10/477,469.

Jan. 14, 2008 Response to Office Action, filed in connection with U.S. Appl. No. 10/477,469.

Apr. 17, 2008 Office Action, issued in connection with U.S. Appl. No. 10/477,469.

Aug. 15, 2008 Request for Continued Examination and Amendment, filed in connection with U.S. Appl. No. 10/477,469.

Nov. 26, 2008 Office Action, issued in connection with U.S. Appl. No. 10/477,469.

Mar. 26, 2009 Response to Office Action, filed in connection with U.S. Appl. No. 10/477,469.

Jun. 12, 2009 Office Action, issued in connection with U.S. Appl. No. 10/477,469.

Nov. 11, 2009 Request for Continued Examination and Amendment, filed in connection with U.S. Appl. No. 10/477,469.

Feb. 1, 2010 Office Action, issued in connection with U.S. Appl. No. 10/477,469.

Aug. 2, 2010 Response to Office Action, filed in connection with U.S. Appl. No. 10/477,469.

Oct. 15, 2010 Office Action, issued in connection with U.S. Appl. No. 10/477,469.

Jun. 17, 2011 Request for Continued Examination and Amendment, filed in connection with U.S. Appl. No. 10/477,469.

Aug. 12, 2011 Preliminary Amendment and Summary of Examiner Interview, filed in connection with U.S. Appl. No. 10/477,469.

Jun. 18, 2012 Office Action and Examiner Interview Summary, issued in connection with U.S. Appl. No. 10/477,469.

Jun. 18, 2012 Response to Office Action and Examiner Interview Summary, filed in connection with U.S. Appl. No. 10/477,469.

Jun. 25, 2012 Examiner Interview Summary and Notice of Allowance, issued in connection with U.S. Appl. No. 10/477.469.

Jan. 8, 2013 Office Action, issued in connection with U.S. Appl. No. 13/651,250.

Apr. 17, 2013 Response to Office Action, filed in connection with U.S. Appl. No. 13/651,250.

Apr. 26, 2013 Office Action, issued in connection with U.S. Appl. No. 13/651,250.

Jun. 12, 2013 Response, filed in connection with U.S. Appl. No. 13/651,250.

Jun. 21, 2013 Notice of Allowance, issued in connection with U.S. Appl. No. 13/651,250.

Banzone, J. A. et al., (1995) "Histidine-254 is essential for the inactivation of phosphotriesterase with the alkynyl phosphate esters and diethyl pyrocarbonate," Biochemistry 34:750-754.

Benning, M. M. et al., (1994) "Three-dimensional structure of phosphotriesterase: An enzyme capable of detoxifying organophosphate nerve agents," Biochemistry 33:15001-15007.

Benning, M.M. et al. (1995) "Three-Dimensional Structure of the Binuclear Metal Center for Phosphotriesterase"; Biochemistry 34:7973-7978.

Benning, M.M. et al. (2000) "The Binding of Substrate Analogs to Phosphotriesterase"; J. Biol. Chem. 275(39):30556-30560.

Benning, M.M. et al., (2001) "High resolution x-ray structures of different metal-substituted forms of phosphotriesterase from *Pseudomonas diminuta*," Biochemistry 40:2712-2722.

Billecke, 5.5. et al. (1999) "Characterization of a soluble mouse liver enzyme capable of hydrolyzing diisopropyl phosphorofluoridate"; Chem. Biol. Interact. 119-120:251-256.

Broomfield, C.A. et al. (1999) "Protein engineering of a human enzyme that hydrolyzes V and G nerve agents: design, construction and characterization"; Chem. Biol. Interact. 119-120:413-418.

Buchbinder, J.L. et al. (1998) "Biochemical Characterization and Crystallographic Structure of an *Escherichia coli* Protein from the Phosphotriesterase Gene Family"; Biochemistry 37:5096-5160.

Caldwell, S. R. et al., (1991) "Limits of diffusion in the hydrolysis of substrates by the phosphotriesterase from *Pseudomonas diminuta*," Biochemistry 30:7438-7444.

Campbell, P.M. et al. (1998) "Two different amino acid substitutions in the ali-esterase, E3, confer alternative types of organophosphorus insecticide resistance in the sheep blowfly, *Lucilia cuprina*"; Insect Biochemistry and Molecular Biology 28: 139-150.

Chen-Goodspeed, M. et al., (2001) "Structural determinants of the substrate and stereochemical specificity of phosphotriesterase," Biochemistry 40: 1325-1331.

Chen-Goodspeed, M. et al., (2001) "Enhancement, relaxation, and reversal of the stereoselectivity for phosphotriesterase by rational evolution of active site residues," Biochemistry 40: 1332-1339.

Cheng, T. et al. (1999) "*Alteromonas* prolidase for organophosphorus G-agent decontamination"; Chem. Biol. Interact. 119-120:455-462.

Cho, C.M.-H. et al., (2002) "Bacterial cell surface display of organophosphorus hydrolase for selective screening of improved hydrolysis of organophosphate nerve agents," Applied and Environmental Microbiology 68(4):2026-2030.

Claudianos, C. et al. (1999) "The same amino acid substitution in orthologous esterases confers organophosphate resistance on the house fly and a blowfly"; Insect Biochemistry and Molecular Biology 29:675-686.

Cook, A.M. et al. (1978) "Phosphorus-Containing Pesticide Breakdown Products: Quantitative Utilization as Phosphorus Sources by Bacteria"; Applied and Environ. Microbiol. 36(5):668-672.

Davies, J.A. et al. (1997) "Molecular cloning and expression pattern of rpr-1, a resiniferatoxin-binding, phosphotriesterase-related protein, expressed in rat kidney tubules"; FEBS Letters 410:378-382.

DiSoudi, B. et al. (1999) "Modification of Near Active Site Residues in Organophosphorus Hydrolase Reduces Metal Stoichiometry and Alters Substrate Specificity"; Biochemistry 38:2866-2872.

DiSioudi, B. D. et al., (1999) "Rational design of organophosphorus hydrolase for altered substrate specificities," Chemico-Biological Interactions 119-120:211, 223.

Donarski, W. J. et al., (1989) "Structure-activity relationships in the hydrolysis of substrates by the phosphotriesterase from *Pseudomonas diminuta*," Biochemistry 28:4650-4655.

Doorn, J.A. et al. (1999) "Evidence that several conserved histidine residues are required for hydrolytic activity of human paraoxonase/arylesterase"; Chem. Biol. Interact. 120:235-241.

Dumas, D. P. et al. (1989) "Purification and Properties of the Phosphotriesterase from *Pseudomonas diminuta*"; J. Biol. Chem. 264:19659-19665.

(56) References Cited

OTHER PUBLICATIONS

Dumas, D.P. et al. (1990) "Expression of Pseudomonas phosphotriesterase activity in the fall armyworm confers resistance to insecticides"; Experientia 46:729-731.

Dumas, D.P. et al. (1989) "Diisopropylfluorophosphate Hydrolysis by a Phosphotriesterase from *Pseudomonas diminuta*"; Biotechnol. Appl. Biochem. 11 :235-243.

Elashvili, I. et al. (1998) "phnE and glpT Genes Enhance Utilization of Organophosphates in *Escherichia coli* K-12"; Applied and Environ. Microbiol. 64(7):2601-2608.

Gan, K.N. et al. (1991) "Purification of Human Serum Paraoxonase/Arylesterase: Evidence for One Esterase Catalyzing Both Activities"; Drug Metabolism and Disposition 19(1):100-106.

Gardiner, A.T. et al. (1996) "The purple photosynthetic bacterium *Rhodopseudomonas acidophila* contains multiple puc peripheral antenna complex (LH2) genes: Cloning and initial characterisation of four β/α pairs" Photosyn. Res. 49:223-2235.

Ghisalba, O. et al., (1987) "Microbial degradation and utilization of selected organophosphorus compounds—stragegies and applications," CHIMIA 41 (6):206-215.

Gopal, S. et al., (2000) "Mutagenesis of organophosphorus hydrolase to enhance hydrolysis of the nerve agent VX," Biochemical and Biophysical Research Communications 279:516-519.
Grimsley, J. K. et al., (1997) "Organophosphorus hydrolase is a remarkably stable enzyme that unfolds through a homodimeric intermediate," Biochemistry 36:14366-14374.
Harcourt, R.L. et al. (2002) "Development of a simple and sensitive fluorimetric method for isolation of coumaphos-hydrolysing bacteria"; Letters in Appl. Microbiol. 34:263-268.
Harel, M. et al., (1992) "Conversion of acetylcholinesterase to butyrylcholinesterase: Modeling and mutagenesis," Proc. Natl. Acad. Sci. USA 89:10827-10831.
Harper, L.L. et al. (1988) "Dissimilar Plasmids Isolated from *Pseudomonas diminuta* MG and a *Flavobacterium* sp. (ATCC 27551) Contain Identical opd Genes"; Applied and Environmental Microbiology 54:2586-2589.
Havens, P.L. et al. "Reusable Immobilized Enzyme/Polyurethane Sponge for Removal and Detoxification of Localized Organophosphate Pesticide Spills"; Industrial & Engineering Chemistry Research, American Chemical Society, Washington, U.S. (1993) 32:2254-2258.
Hong, S.-B. et al., (1996) "Metal-substrate interactions facilitate the catalytic activity of the bacterial phosphotriesterase," Biochemistry 35: 10904-1 0912.
Hong, S.B. et al. (1999) "Stereochemical preferences for chiral substrates by the bacterial phosphotriesterase"; Chem. Biol. Interact. 120:225-234.
Hong, S.-B. et al., (1999) "Stereochemical constraints on the substrate specificity of phosphotriesterase," Biochemistry 38:1159-1165.
Horne, I. et al. "Identification of an opd (Organophosphate Degradation) Gene in an *Agrobacterium* Isolate"; Applied and Environmental Microbiology (Jul. 2002) 68(7):3371-3376.
Hoskin, F.C.G. et al. (1999) "Organophosphorus acid anhydrolase in slime mold duckweek and mung bean: a continuing search for a physiological role and a natural substrate"; Chem. Biol. Interact. 120:399-404.
Ibrahim, F.B. et al. (1966) "Ultraviolet Spectrophotometric Method for Fenthion"; J. Agr. Food Chem. 14(4):369-371.
Jackson, C. J. et al., (2009) "Structure-based rational design of a phosphotriesterase," Applied and Environmental Microbiology 75(15):5153-5156.
Kuo, J. M. et al., (1994) "Identification of the histidine ligands to the binuclear metal center of phosphotriesterase by site-directed mutagenesis," Biochemistry 33:4265-4272.
Kuo, J. M. et al., (1997) "Perturbations to the active site of phosphotriesterase," Biochemistry 36:1982-1988.
Lai, K. et al. (1995) "Characterization of P—S Bond Hydrolysis in Organophosphorothioate Pesticides by Organophosphorus Hydrolase"; Archives of Biochem. and Biophysics 318:59-64.
LeJeune, K.E. et al. (1998) "Nerve agents degraded by enzymatic foams"; Nature 395:27-28.
Li, W.-S. et al., (2001) "Stereoselective detoxification of chiral sarin and soman analogues by phosphotriesterase," Bioorganic & Medicinal Chemistry 9:2083-2091.
Liu, W. et al., (1992) "Enhancement of the chemical and antimicrobial properties of subtilin by site-directed mutagenesis," Journal of Biological Chemistry 267(35):25078-25085.
McAuliffe, K. S. et al., (1990) "Glyphosate degradation by *Agrobacterium radiobacter* isolated from activated sludge," J Industrial Microbiology 6:219-221.
Muh, U. et al., (1994) "Lactate monooxygenase. I. Expression of the mycobacterial gene in *Escherichia coli* and site-directed mutagenesis of lysine 266," Journal of Biological Chemistry 269(11):7982-7988.
Mulbry, W.W. (1992) "The aryldialkylphosphatase-encoding gene adpB from *Nocardia* sp. strain B-1: cloning, sequencing and expression in *Escherichia coli*"; Gene 121:149-153.
Mulbry, W.W. et al. (1989) "Parathion Hydrolase Specified by the *Flavobacterium* opd Gene: Relationship between the Gene and Protein"; J. of Bact. 171(12):6740-6746.
Mulbry, W.W. et al. (19911 "Degradation of pesticides by microorganisms and the potential for genetic manipulation"; Crop Protection 10:334-345.
Munnecke, D.M. et al. (1976) "Pathways of Microbial Metabolism of Parathion"; Applied & Environ. Microbiol. 31(1):63-69.
Newcomb, R.D. et al. (1997) "A single amino acid substitution coverts a carboxylesterase to an organophosphorus hydrolase and confers insecticide resistance on a blowfly"; Proc. Nat. Acad. Sci. USA 94:7464-7468.
Raushel, F. M., (2002) "Bacterial detoxification of organophosphate nerve agents," Current Opinion in Microbiology 5:288-295.
Rekha, K. et al. (2000) "Biosensors for the Detection of Organophosphorous Pesticides"; Biotechnology 20(3):213-235.
Rosenberg, A. et al. (1979) "Microbial Cleavage of Various Organophosphorus Insecticides"; Applied & Environ. Microbiol. 37(5):886-891.
Roth, M. (1969) "Fluorimetric Assay of Enzymes"; Methods of Biochemical Analysis 17:189-285.
Scanlan, T.S. et al. (1995) "Evolution in Action"; Chem. and Biol. 2(2):71-75.
Schwede, T. et al., (2003) "Swiss-Model: an automated protein homology-modeling server," Nucleic Acids Research 31 (13):3381-3385.
Serdar, C.M. et al. (1989) "Parathion hydrolase gene from *Pseudomonas diminuta* MG: subcloning, complete nucleotide sequence, and expression of the mature portion of the enzyme in *Escherichia coli*"; Biotechnology 7: 1151-1155.
Shim, H. et al., (1998) "Hydrolysis of phosphodiesters through transformation of the bacterial phosphotriesterase," Journal of Biological Chemistry 273(28):17445-17450.
Shim, H. et al., (2000) "Self-assembly of the binuclear metal center of phosphotriesterase," Biochemistry 39:7357-7364.
Simon, I. et al., (2001) "Predicting protein conformation by statistical methods," Biochimica et Biophysica Acta 1549:123-136.
Sorenson, R.C. et al. (1995) "Reconsideration of the catalytic center and mechanism of mammalian paraoxonase/arylesterase"; Proc. Nat. Acad. Sci. USA 92:7187-7191.
Sogorb, M.A. and Vilanova, E., (2002) "Enzymes involved in the detoxification of organophosphorus, carbamate and pyrethroid insecticides through hydrolysis," Toxicology Letters 128:215-228.
Vanhooke, J. L. et al., (1996) "Three-dimensional structure of the zinc-containing phosphotriesterase with the bound substrate analog diethyl 4-methylbenzylphosphonate," Biochemistry 35:6020-6025.
Wackett, L. P. et al., (1987) Bacterial carbon-phosphorus lyase: Products, rates, and regulation of phosphonic and phosphinic acid metabolism, J Bacteriology 169(2):710-717.
Wang, Q. et al. (1998) "Purification and Properties of Soman-Hydrolyzing Enzyme from Human Liver"; J. Biochem. and Molecular Toxicology 12(4):213-217.
Wang, F. et al. (1993) "Purification and Properties of a Diisopropyl-Fluorophosphatase from Squid *Todarodes Pacificus* Steenstrup"; J. Biochern. Toxicology 8(3):161-166.

(56) References Cited

OTHER PUBLICATIONS

Watkins, L. M. et al. (1997) "Augmented hydrolysis of diisopropyl fluorophosphate in engineered mutant of phosphotriesterase," Journal of Biological Chemistry 272(41):25596-25601.
Wu, F. et al., (2000) "Rationally engineered mutants of phosphotriesterase for preparative scale isolation of chiral organophosphates," J. Am. Chem. Soc. 122:10206-10207.
Yang, F. et al. (1995) "Nonaqueous Biocatalytic Degradation of a Nerve Gas Mimic"; Biotechnol. Prog. 11:471-474.
Zimmerer, R.P. et al. (1996) "Isolation and Morphology of Temperate *Agrobacterium tumefaciens* Bacteriophage"; J. Bacteriol. 92(3):746-750.
Islam et al. (2010). Organophosphorus Hydrolase (OpdB) of *Lactobacillus brevis* WCP902 from Kimchi Is Able to Degrade Organophosphorus Pesticides. *Journal of Agricultural and Food Chemistry*, 58(9), 5380-5386.
Jackson et al. (2009). Conformational sampling, catalysis, and evolution of the bacterial phosphotriesterase. *PNAS*, 106(51), 21631-21636.
Jackson et al. (2008). In Crystallo Capture of a Michaelis Complex and Product-binding Modes of a Bacterial Phosphotriesterase. *Journal of Molecular Biology*, 375, 1189-1196.
Jackson et al. (2005). The structure of an enzyme-product complex reveals the critical role of a terminal hydroxide nucleophile in the bacterial phosphotriesterase mechanism. *Biochimica et Biophysica Acta*, 1752, 56-64.
Yang et al. (2003). Evolution of an organophosphate-degrading enzyme: a comparison of natural and directed evolution. *Protein Engineering*, 16(2), 135-145.
International Search Report, dated Oct. 17, 2012 in connection with PCT International Application No. PCT/AU2012/000869, filed Jul. 20, 2012.
Written Opinion of the International Searching Authority, dated Oct. 17, 2012 in connection with PCT International Application No. PCT/AU2012/000869, filed Jul. 20, 2012.
International Preliminary Report on Patentability (Chapter I of the Patent Cooperation Treaty), including Written Opinion of the International Searching Authority, dated Jan. 21, 2014 by the International Bureau of WIPO in connection with PCT International Application No. PCT/AU2012/000869, filed Jul. 20, 2012.
Extended European Search Report and Written Opinion dated Nov. 20, 2014 in connection with European Application No. 12815284.0.
Abdullah et al., *Biotechnology* 4:1087-90 (1986).
Afriat et al., *Biochemistry* 45:13677-86 (2006).
Barron and Woodburn, *Reviews of Environmental Contamination and Toxicology* 144:1-93 (1995).
Cadwell and Joyce, *PCR Methods and Applications* 2:28-33 (1992).
Capecchi, *Cell* 22:479-488 (1980).
Cheng et al., *Plant Cell Reports* 15:653-657 (1996).
Cho et al., *Appl. Environ. Microbiol.* 70:4681-85 (2004).
Clapp, *Clin. Perinatol.* 20:155-168 (1993).
Coco et al., *Nature Biotechnology* 19:354-359 (2001).
Coco et al., *Nature Biotechnology* 20:1246-50 (2002).
Crameri et al., *Nature* 391:288-291 (1998).
Curiel et al., *Human Gene Therapy* 3:147-154 (1992).
Dong et al., *J. Mol. Biol.* 353:655-663 (2005).
Eggert et al., *Chembiochem* 6:1062-67 (2005).
Eglitis et al., *Biotechniques* 6:608-614 (1988).
Fujimura et al., *Plant Tissue Culture Letters* 2:74-75 (1985).
Gordon et al., *Chemico-Biological Interactions* 119-120:463-470 (1999).
Graham and Van der eb, *Virology* 54:536-539 (1973).
Grant et al., *Plant Cell Reports* 15:254-258 (1995).
Habig et al., *J. Biol. Chem.* 249:7130-39 (1974).
Harayama, *Trends in Biotechnology* 16:76-82 (1998).
Hellinga, *Proc. Natl. Acad. Sci. USA* 94:10015-17 (1997).
Horne et al., *FEMS Microbiology Letters* 222:1-8 (2003).
Horne et al., *FEMS Microbiology Letters* 259:187-194 (2006).
Jackson et al., *Biochem. J.* 397:501-508 (2006).
Jezequel et al., *Biotechniques* 45:523-532 (2008).
Koziel et al., *Plant Mol. Biol.* 32:393-405 (1996).
Leung et al., *Technique* 1:11-15 (1989).
Lu et al., *J. Exp. Med.* 178:2089-96 (1993).
Mayer and Ellersieck, Manual of Acute Toxicology (1986).
Needleman and Wunsch, *J. Mol. Biol.* 48:443-453 (1970).
Ness et al., *Nature Biotechnology* 20:1251-55 (2002).
Ostermeier et al., *Nature Biotechnology* 17:1205-09 (1999).
Petrikovics et al., *Toxicological Sciences* 57:16-21 (2000).
Petrikovics et al., *Drug Delivery* 7:83-89 (2000).
Russell et al., *Australian Biotechnology* 11:24-26 (2001).
Sieber et al., *Nature Biotechnology* 19:456-460 (2002).
Stemmer, *Proc. Natl. Acad. Sci. USA* 91:10747-51 (1994).
Stemmer, *Nature* 370:389-391 (1994).
Toriyama et al., *Theor. Appl. Genet.* 73:16-19 (1986).
Volkov et al., *Nucleic Acids Research* 27(18):e18 (1999).
Wagner et al., *Proc. Natl. Acad. Sci. USA* 89:6099-103 (1992).
Yair et al., *Critical Reviews in Biotechnology* 28:265-275 (2008).
Zhao et al., *Nature Biotechnology* 16:258-261 (1998).

\* cited by examiner

SEQUENCE LISTING

<160> NUMBER OF SEQ ID NOS: 7

<210> SEQ ID NO 1
<211> LENGTH: 356

<212> TYPE: PRT
<213> ORGANISM: Artificial Sequence
<220> FEATURE:
<223> OTHER INFORMATION: Mutant OpdA enzyme (A900)

<400> SEQUENCE: 1

```
Pro Ile Gly Thr Gly Asp Leu Ile Asn Thr Val Arg Gly Pro Ile Pro
1               5                   10                  15

Val Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Lys
        35                  40                  45

Ala Leu Val Glu Lys Ala Val Arg Gly Leu Arg His Ala Arg Ala Ala
    50                  55                  60

Gly Val Gln Thr Ile Val Asp Val Ser Thr Phe Asp Ile Gly Arg Asp
65                  70                  75                  80

Val Arg Leu Leu Ala Glu Val Ser Arg Ala Ala Asp Val His Ile Val
                85                  90                  95

Ala Ala Thr Gly Leu Trp Phe Asp Pro Pro Leu Ser Met Arg Met Arg
            100                 105                 110

Ser Val Glu Glu Leu Thr Gln Phe Phe Leu Arg Glu Ile Gln His Gly
        115                 120                 125

Ile Glu Asp Thr Gly Ile Arg Ala Gly Ile Ile Lys Val Ala Thr Thr
    130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Ser Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Glu Asp Thr Asp Asp Leu
        195                 200                 205

Ser Tyr Leu Thr Gly Leu Ala Ala Arg Gly Tyr Leu Val Gly Leu Asp
    210                 215                 220

Arg Met Pro Tyr Ser Ala Ile Gly Leu Glu Gly Asp Ala Ser Ala Leu
225                 230                 235                 240

Ala Leu Phe Gly Thr Arg Ser Trp Gln Thr Arg Ala Leu Leu Ile Lys
                245                 250                 255

Ala Leu Ile Asp Arg Gly Tyr Lys Asp Arg Ile Leu Val Ser His Asp
            260                 265                 270

Trp Leu Phe Gly Phe Ser Ser Tyr Val Thr Asn Ile Met Asp Val Met
        275                 280                 285

Asp Arg Ile Asn Pro Asp Gly Met Ala Phe Val Pro Leu Arg Val Ile
    290                 295                 300

Pro Phe Leu Arg Glu Lys Gly Val Pro Pro Glu Thr Leu Ala Gly Val
305                 310                 315                 320

Thr Val Ala Asn Pro Ala Arg Phe Leu Ser Pro Thr Val Arg Ala Val
                325                 330                 335

Val Thr Arg Ser Glu Thr Ser Arg Pro Ala Ala Pro Ile Pro Arg Gln
            340                 345                 350

Asp Thr Glu Arg
        355
```

<210> SEQ ID NO 2
<211> LENGTH: 357

<212> TYPE: PRT
<213> ORGANISM: Artificial Sequence
<220> FEATURE:
<223> OTHER INFORMATION: Native OpdA without signal sequence and with N-terminal Met

<400> SEQUENCE: 2

Met Pro Ile Gly Thr Gly Asp Leu Ile Asn Thr Val Arg Gly Pro Ile
1               5                   10                  15
Pro Val Ser Glu Ala Gly Phe Thr Leu Thr His Glu His Ile Cys Gly
            20                  25                  30
Ser Ser Ala Gly Phe Leu Arg Ala Trp Pro Glu Phe Gly Ser Arg
        35                  40                  45
Lys Ala Leu Ala Glu Lys Ala Val Arg Gly Leu Arg His Ala Arg Ser
    50                  55                  60
Ala Gly Val Gln Thr Ile Val Asp Val Ser Thr Phe Asp Ile Gly Arg
65                  70                  75                  80
Asp Val Arg Leu Leu Ala Glu Val Ser Arg Ala Ala Asp Val His Ile
                85                  90                  95
Val Ala Ala Thr Gly Leu Trp Phe Asp Pro Pro Leu Ser Met Arg Met
            100                 105                 110
Arg Ser Val Glu Glu Leu Thr Gln Phe Phe Leu Arg Glu Ile Gln His
        115                 120                 125
Gly Ile Glu Asp Thr Gly Ile Arg Ala Gly Ile Ile Lys Val Ala Thr
130                 135                 140
Thr Gly Lys Ala Thr Pro Phe Gln Glu Leu Val Leu Lys Ala Ala Ala
145                 150                 155                 160
Arg Ala Ser Leu Ala Thr Gly Val Pro Val Thr Thr His Thr Ser Ala
                165                 170                 175
Ser Gln Arg Asp Gly Glu Gln Gln Ala Ala Ile Phe Glu Ser Glu Gly
            180                 185                 190
Leu Ser Pro Ser Arg Val Cys Ile Gly His Ser Asp Asp Thr Asp Asp
        195                 200                 205
Leu Ser Tyr Leu Thr Gly Leu Ala Ala Arg Gly Tyr Leu Val Gly Leu
210                 215                 220
Asp Arg Met Pro Tyr Ser Ala Ile Gly Leu Glu Gly Asn Ala Ser Ala
225                 230                 235                 240
Leu Ala Leu Phe Gly Thr Arg Ser Trp Gln Thr Arg Ala Leu Leu Ile
                245                 250                 255
Lys Ala Leu Ile Asp Arg Gly Tyr Lys Asp Arg Ile Leu Val Ser His
            260                 265                 270
Asp Trp Leu Phe Gly Phe Ser Ser Tyr Val Thr Asn Ile Met Asp Val
        275                 280                 285
Met Asp Arg Ile Asn Pro Asp Gly Met Ala Phe Val Pro Leu Arg Val
290                 295                 300
Ile Pro Phe Leu Arg Glu Lys Gly Val Pro Pro Glu Thr Leu Ala Gly
305                 310                 315                 320
Val Thr Val Ala Asn Pro Ala Arg Phe Leu Ser Pro Thr Val Arg Ala
                325                 330                 335
Val Val Thr Arg Ser Glu Thr Ser Arg Pro Ala Ala Pro Ile Pro Arg
            340                 345                 350
Gln Asp Thr Glu Arg
        355

<210> SEQ ID NO 3

<211> LENGTH: 357
<212> TYPE: PRT
<213> ORGANISM: Artificial Sequence
<220> FEATURE:
<223> OTHER INFORMATION: Mutant OpdA enzyme (M4)

<400> SEQUENCE: 3

Met Pro Ile Gly Thr Gly Asp Leu Ile Asn Thr Val Arg Gly Pro Ile
1               5                   10                  15

Pro Val Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg His Ala Arg Ser
50                  55                  60

Ala Gly Val Gln Thr Ile Val Asp Val Ser Thr Phe Asp Ile Gly Arg
65                  70                  75                  80

Asp Val Arg Leu Leu Ala Glu Val Ser Arg Ala Ala Asp Val His Ile
                85                  90                  95

Val Ala Ala Thr Gly Leu Trp Phe Asp Pro Pro Leu Ser Met Arg Met
            100                 105                 110

Arg Ser Val Glu Glu Leu Thr Gln Phe Phe Leu Arg Glu Ile Gln His
        115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ser Ala
                165                 170                 175

Ser Gln Arg Gly Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Gly Leu Ala Ala Arg Gly Tyr Leu Val Gly Leu
210                 215                 220

Asp Arg Met Pro Tyr Ser Ala Ile Gly Leu Glu Gly Asp Ala Ser Ala
225                 230                 235                 240

Leu Ala Leu Phe Gly Asn Arg Ser Trp Gln Thr Arg Ala Leu Leu Ile
                245                 250                 255

Lys Ala Leu Ile Asp Arg Gly Tyr Lys Asp Arg Ile Leu Val Ser His
            260                 265                 270

Asp Trp Leu Phe Gly Phe Ser Ser Tyr Val Thr Asn Ile Met Asp Val
        275                 280                 285

Met Asp Arg Ile Asn Pro Asp Gly Met Ala Phe Val Pro Leu Arg Val
290                 295                 300

Ile Pro Phe Leu Arg Glu Lys Gly Val Pro Pro Glu Thr Leu Ala Gly
305                 310                 315                 320

Val Thr Val Ala Asn Pro Ala Arg Phe Leu Ser Pro Thr Val Arg Ala
                325                 330                 335

Val Val Thr Arg Ser Glu Thr Ser Arg Pro Ala Ala Pro Ile Pro Arg
            340                 345                 350

Gln Asp Thr Glu Arg
        355

<210> SEQ ID NO 4

```
<211> LENGTH: 333
<212> TYPE: PRT
<213> ORGANISM: Artificial Sequence
<220> FEATURE:
<223> OTHER INFORMATION: OPH miunus signal sequence and with N-terminal
      Met

<400> SEQUENCE: 4

Met Gly Asp Arg Ile Asn Thr Val Arg Gly Pro Ile Thr Ile Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Lys Ala Leu Ala
        35                  40                  45

Glu Lys Ala Val Arg Gly Leu Arg Arg Ala Arg Ala Ala Gly Val Arg
50                  55                  60

Thr Ile Val Asp Val Ser Thr Phe Asp Ile Gly Arg Asp Val Ser Leu
65                  70                  75                  80

Leu Ala Glu Val Ser Arg Ala Ala Asp Val His Ile Val Ala Ala Thr
                85                  90                  95

Gly Leu Trp Phe Asp Pro Pro Leu Ser Met Arg Leu Arg Ser Val Glu
            100                 105                 110

Glu Leu Thr Gln Phe Phe Leu Arg Glu Ile Gln Tyr Gly Ile Glu Asp
        115                 120                 125

Thr Gly Ile Arg Ala Gly Ile Ile Lys Val Ala Thr Thr Gly Lys Ala
130                 135                 140

Thr Pro Phe Gln Glu Leu Val Leu Lys Ala Ala Arg Ala Ser Leu
145                 150                 155                 160

Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Ile Gly Leu Asp His Ile Pro
210                 215                 220

His Ser Ala Ile Gly Leu Glu Asp Asn Ala Ser Ala Ser Ala Leu Leu
225                 230                 235                 240

Gly Ile Arg Ser Trp Gln Thr Arg Ala Leu Leu Ile Lys Ala Leu Ile
                245                 250                 255

Asp Gln Gly Tyr Met Lys Gln Ile Leu Val Ser Asn Asp Trp Leu Phe
            260                 265                 270

Gly Phe Ser Ser Tyr Val Thr Asn Ile Met Asp Val Met Asp Arg Val
        275                 280                 285

Asn Pro Asp Gly Met Ala Phe Ile Pro Leu Arg Val Ile Pro Phe Leu
290                 295                 300

Arg Glu Lys Gly Val Pro Gln Gly Thr Leu Ala Gly Ile Thr Val Thr
305                 310                 315                 320

Asn Pro Ala Arg Phe Leu Ser Pro Thr Leu Arg Ala Ser
                325                 330

<210> SEQ ID NO 5
<211> LENGTH: 357
<212> TYPE: PRT
<213> ORGANISM: Artificial Sequence
<220> FEATURE:
<223> OTHER INFORMATION: A900 with N-terminal Met
```

<400> SEQUENCE: 5

| | | | | | | | | | | | | | | |
|---|---|---|---|---|---|---|---|---|---|---|---|---|---|---|
|Met|Pro|Ile|Gly|Thr|Gly|Asp|Leu|Ile|Asn|Thr|Val|Arg|Gly|Pro|Ile
1| | | |5| | | | |10| | | | |15| |

Pro Val Ser Glu Ala Gly Phe Thr Leu Thr His Glu His Ile Cys Gly
              20                  25                  30

Ser Ser Ala Gly Phe Leu Arg Ala Trp Pro Glu Phe Gly Ser Arg
          35                40                  45

Lys Ala Leu Val Glu Lys Ala Val Arg Gly Leu Arg His Ala Arg Ala
50                  55                  60

Ala Gly Val Gln Thr Ile Val Asp Val Ser Thr Phe Asp Ile Gly Arg
65                70                75              80

Asp Val Arg Leu Leu Ala Glu Val Ser Arg Ala Ala Asp Val His Ile
              85                  90              95

Val Ala Ala Thr Gly Leu Trp Phe Asp Pro Pro Leu Ser Met Arg Met
            100               105             110

Arg Ser Val Glu Glu Leu Thr Gln Phe Phe Leu Arg Glu Ile Gln His
          115               120             125

Gly Ile Glu Asp Thr Gly Ile Arg Ala Gly Ile Ile Lys Val Ala Thr
130               135               140

Thr Gly Lys Ala Thr Pro Phe Gln Glu Leu Val Leu Arg Ala Ala Ala
145                 150             155            160

Arg Ala Ser Leu Ala Thr Gly Val Pro Val Thr Thr His Thr Ser Ala
              165             170             175

Ser Gln Arg Asp Gly Glu Gln Gln Ala Ala Ile Phe Glu Ser Glu Gly
          180               185             190

Leu Ser Pro Ser Arg Val Cys Ile Gly His Ser Glu Asp Thr Asp Asp
          195               200             205

Leu Ser Tyr Leu Thr Gly Leu Ala Ala Arg Gly Tyr Leu Val Gly Leu
210               215               220

Asp Arg Met Pro Tyr Ser Ala Ile Gly Leu Glu Gly Asp Ala Ser Ala
225                 230             235            240

Leu Ala Leu Phe Gly Thr Arg Ser Trp Gln Thr Arg Ala Leu Leu Ile
              245             250             255

Lys Ala Leu Ile Asp Arg Gly Tyr Lys Asp Arg Ile Leu Val Ser His
          260               265             270

Asp Trp Leu Phe Gly Phe Ser Ser Tyr Val Thr Asn Ile Met Asp Val
          275               280             285

Met Asp Arg Ile Asn Pro Asp Gly Met Ala Phe Val Pro Leu Arg Val
          290               295             300

Ile Pro Phe Leu Arg Glu Lys Gly Val Pro Pro Glu Thr Leu Ala Gly
305               310               315            320

Val Thr Val Ala Asn Pro Ala Arg Phe Leu Ser Pro Thr Val Arg Ala
              325             330             335

Val Val Thr Arg Ser Glu Thr Ser Arg Pro Ala Ala Pro Ile Pro Arg
          340               345             350

Gln Asp Thr Glu Arg
          355

<210> SEQ ID NO 6
<211> LENGTH: 1071
<212> TYPE: DNA
<213> ORGANISM: Artificial Sequence
<220> FEATURE:
<223> OTHER INFORMATION: Coding sequence for A900

```
<400> SEQUENCE: 6
ccaatcggta caggcgatct gattaatact gttcgcggcc ccattccagt ttcggaagcg      60
ggcttcacac tgacccatga gcatatctgc ggcagttcgg cgggattcct acgtgcgtgg     120
ccggagtttt tcggtagccg caaagctcta gttgaaaagg ctgtgagagg attacgccat     180
gccagagcgg ctggcgtgca aaccatcgtc gatgtgtcga ctttcgatat cggtcgtgac     240
gtccgtttat tggccgaagt ttcgcgggcc gccgacgtgc acatcgtggc ggcgactggc     300
ttatggttcg acccgccact tcaatgcga atgcgcagcg tcgaagaact gacccagttc      360
ttcctgcgtg aaatccaaca tggcatcgaa gacaccggta ttagggcggg cattatcaag     420
gtcgcgacca cagggaaggc gaccccctt caagagttgg tgttacgtgc agccgcgcgg      480
gccagcttgg ccaccggtgt tccggtaacc actcacacgt cagcaagtca gcgcgatggc     540
gagcagcagg cagccatatt tgaatccgaa ggtttgagcc cctcacgggt ttgtatcggt     600
cacagcgaag atactgacga tttgagctac ctaaccggcc tcgctgcgcg cggatacctc     660
gtcggtttag atcgcatgcc gtacagtgcg attggtctag aaggcgatgc gagtgcatta    720
gcgctctttg gtactcggtc gtggcaaaca agggctctct tgatcaaggc gctcatcgac    780
cgaggctaca aggatcgaat cctcgtctcc catgactggc tgttcgggtt ttcgagctat    840
gtcacgaaca tcatggacgt aatggatcgc ataaacccag atggaatggc cttcgtccct    900
ctgagagtga tcccattcct acgagagaag ggcgtcccgc cggaaacgct agcaggcgta    960
accgtggcca atcccgcgcg gttcttgtcc ccgaccgtgc gggccgtcgt gacacgatct  1020
gaaacttccc gccctgccgc gcctattccc cgtcaagata ccgaacgatg a           1071

<210> SEQ ID NO 7
<211> LENGTH: 27
<212> TYPE: PRT
<213> ORGANISM: Artificial Sequence
<220> FEATURE:
<223> OTHER INFORMATION: TAT signal peptide

<400> SEQUENCE: 7

Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
            20                  25
```

ENZYMES FOR DEGRADING ORGANOPHOSPHATES

CROSS-REFERENCE TO RELATED APPLICATIONS

This application is a §371 national stage of PCT International Application No. PCT/AU2012/000869, filed Jul. 20, 2012, claiming the benefit of U.S. Provisional Application Nos. 61/510,337, filed Jul. 21, 2011, and 61/509,810, filed Jul. 20, 2011, the contents of each of which are hereby incorporated by reference in their entirety.

REFERENCE TO SEQUENCE LISTING

This application incorporates-by-reference nucleotide and/or amino acid sequences which are present in the file named "140 724 2251_83133_A_PCT_US_Substitute_Sequence_ Listing_JR.txt," which is 17.5 Kilobytes in size, and which was created May 22, 2014 in the IBM-PC machine format, having an operating system compatibility with MS-Windows, which is contained in the text file filed Jul. 24, 2014 as part of this application.

FIELD OF THE INVENTION

This invention relates to enzymes capable of hydrolysing organophosphate (OP) molecules.

BACKGROUND OF THE INVENTION

Residues of organophosphate (OP) insecticides are undesirable contaminants of the environment and a range of commodities. Areas of particular sensitivity include contamination of soil, irrigation tailwater that is re-cycled, used by irrigators downstream or simply allowed to run off-farm, and residues above permissible levels in agricultural and horticultural exports. Poisoning with organophosphates presents a problem for agricultural workers that are exposed to these chemicals, as well as military personnel exposed to organophosphates used in chemical warfare. Furthermore, the stockpiling of organophosphorus nerve agents has resulted in the need to detoxify these stocks. Bioremediation strategies are therefore required for eliminating or reducing these organophosphate residues and/or stockpiles.

One proposed strategy involves the use of enzymes capable of immobilising or degrading the organophosphate residues. Such enzymes may be employed, for example, in bioreactors through which contaminated water could be passed, or in washing solutions after post-harvest disinfestation of fruit, vegetables or animal products to reduce residue levels and withholding times. Suitable enzymes for degrading organophosphate residues include OP hydrolases from bacteria (Mulbry, 1992; Mulbry and Kearney, 1991; Cheng et al., 1999; U.S. Pat. Nos. 5,484,728; 5,589,386; Dong et al., 2005), vertebrates (Wang et al., 1993; 1998; Gan et al, 1991; Broomfield et al., 1999) and OP resistant insects (WO 95/19440 and WO 97/19176). It is desirable that the OP hydrolases degrade the organophosphate residues at a rapid rate.

The most thoroughly studied OP degrading enzyme is bacterial organophosphate dihydrolase (termed OPD, OPH or PTE), which is encoded by identical genes on dissimilar plasmids in both *Flavobacterium* sp. ATCC 27551 and *Brevundimonas diminuta* MG (Harper et al., 1988; Mulbry and Karns, 1989). OPD is a homodimeric protein that is capable of hydrolysing a wide range of phosphate triesters (both oxon and thion OPs) (Dumas et al., 1989a, b). Its reaction mechanism directly or indirectly involves metal ions, preferably $Co^{++}$, but also including $Zn^{++}$, $Cd^{++}$, $Fe^{++}$ and other divalent cations. OPD has no detectable activity with phosphate monoesters or diesters (Dumas et al., 1989a, b; 1990).

OPD homologues (phosphotriesterase homology proteins, or PHPs) have been identified in the genomes of *Escherichia coli* (ePHP), *Mycobacterium tuberculosis* (mtPHP) and *Mycoplasma pneumoniae* (mpPHP), although only ePHP has been tested for phosphotriesterase activity (Scanlan and Reid, 1995; Buchbinder et al., 1998). No activity was detected in ePHP crude lysates with any of the substrates tested, such as p-nitrophenyl acetate, bis(p-nitrophenyl) phosphate, paraoxon and p-nitrophenyl phosphate. A class of more distantly related proteins has been identified that has very low levels of OP hydrolase activity, but high levels of lactonase activity, likewise the OPD enzymes have very low levels of lactonse activity (less than 0.001% of the activity against OP substrates) (Afriat et al., 2006).

OPD homologues have also been identified in vertebrates (Davies et al., 1997), although their function in these organisms is unknown. OPD, ePHP, mtPHP and mammalian PHPs are 27-30% identical at the amino acid level, while mpPHP is less similar. Amino acid residues involved in $Zn^{++}$ binding are conserved across the all members of the phosphotriesterase family identified to date (Buchbinder et al., 1998).

More recently, an OP degrading enzyme has been isolated from *Agrobacterium* (WO 02/092803; Horne et al., 2002; Jackson et al., 2009). This enzyme was termed OpdA because it shares about 90% amino acid sequence identity with OPD. Despite the relatedness of OpdA and OPD at the amino acid level, these enzymes have been shown to have varying activities against different OPs.

There is a need for further OP degrading enzymes which can be used in bioremediation strategies. In particular, there is a need for enzymes with enhanced activity against specific OPs that can be used in bioremediation in the field.

SUMMARY OF THE INVENTION

The present inventors have identified polypeptides with improved activity when compared to naturally occurring OpdA.

Thus, in one aspect the present invention provides a polypeptide comprising amino acids whose sequence is:
  i) set forth as SEQ ID NO:1,
  ii) at least 95% identical to the sequence set forth as SEQ ID NO:1, or
  iii) a fragment of i) or ii) which has organophosphate hydrolysing activity and/or which is at least 270 amino acids in length,
    wherein the polypeptide comprises one or more or all of;
    a) a valine at a position corresponding to amino acid number 51 of SEQ ID NO:1,
    b) an alanine at a position corresponding to amino acid number 63 of SEQ ID NO:1,
    c) an arginine at a position corresponding to amino acid number 156 of SEQ ID NO:1,
    d) a glutamic acid at a position corresponding to amino acid number 203 of SEQ ID NO:1, and
    e) an aspartic acid at a position corresponding to amino acid number 236 of SEQ ID NO:1.

In an embodiment, the polypeptide has organophosphate hydrolysing activity.

In another embodiment, the polypeptide has greater organophosphate hydrolysing activity than a second polypeptide whose amino acid sequence is selected from the group consisting of SEQ ID NO:2, SEQ ID NO:3 and SEQ ID NO:4. More preferably, the polypeptide has greater organophosphate hydrolysing activity than a polypeptide whose amino acid sequence is provided as SEQ ID NO:2, a polypeptide whose amino acid sequence is provided as SEQ ID NO:3 and a polypeptide whose amino acid sequence is provided as SEQ ID NO:4.

In a preferred embodiment, a polypeptide of the invention has at least a 2 fold, or 4 fold or 6 fold higher second order rate constant ($k_{cat}/K_m$) for chlorpyrifos methyl than a polypeptide whose amino acid sequence is selected from the group consisting of SEQ ID NO:2, SEQ ID NO:3, and SEQ ID NO:4, preferably all three.

In a preferred embodiment, a polypeptide of the invention has at least a 1.5 fold or 2 fold higher second order rate constant ($k_{cat}/K_m$) for diazinon than a polypeptide whose amino acid sequence is selected from the group consisting of SEQ ID NO:2, SEQ ID NO:3, and SEQ ID NO:4, preferably all three.

In a preferred embodiment, a polypeptide of the invention has at least a 2 fold, or 3 fold or 4 fold higher second order rate constant ($k_{cat}/K_m$) for parathion ethyl than a polypeptide whose amino acid sequence is selected from the group consisting of SEQ ID NO:2, SEQ ID NO:3, and SEQ ID NO:4, preferably all three.

In a preferred embodiment, a polypeptide of the invention has at least a 1.2 fold, or 1.5 fold higher catalytic constant ($k_{cat}$) for chlorpyrifos ethyl than a polypeptide whose amino acid sequence is selected from the group consisting of SEQ ID NO:2, SEQ ID NO:3, and SEQ ID NO:4, preferably all three.

With regard to the above four embodiments, preferably the polypeptide of the invention has the defined activity relative to a polypeptide whose amino acid sequence is provided as SEQ ID NO:2, a polypeptide whose amino acid sequence is provided as SEQ ID NO:3, and a polypeptide whose amino acid sequence is provided as SEQ ID NO:4.

In an embodiment, the organophosphate is an aromatic non-vinyl organophosphate. More preferably, the leaving group of the organophosphate has a pKa of less than 8. In an embodiment, the organophosphate is parathion ethyl, parathion methyl, diazinon, chlorpyrifos ethyl, chlorpyrifos methyl or malathion.

In an embodiment, a polypeptide of the invention has a second order rate constant ($k_{cat}/K_m$) for chlorpyrifos ethyl of at least about $2\times10^6$ $sec^{-1}\cdot M^{-1}$, for chlorpyrifos methyl of at least about $3.5\times10^5$ $sec^{-1}\cdot M^{-1}$, for diazinon of at least about $3.6\times10^6$ $sec^{-1}\cdot M^{-1}$, for parathion ethyl of at least about $9\times10^7$ $sec^{-1}\cdot M^{-1}$, or for parathion methyl of at least about $3\times10^6$ $sec^{-1}\cdot M^{-1}$, or a combination of two or more thereof, preferably all five. More preferably, a polypeptide of the invention has a second order rate constant ($k_{cat}/K_m$) for chlorpyrifos methyl of at least about $3.5\times10^5$ $sec^{-1}\cdot M^{-1}$, for diazinon of at least about $3.6\times10^6$ $sec^{-1}\cdot M^{-1}$, for parathion ethyl of at least about $9\times10^7$ $sec^{-1}\cdot M^{-1}$, or a combination of two or more thereof, preferably all three.

In another aspect, the present invention provides a polypeptide which hydrolyses an organophosphate molecule and which has a second order rate constant ($k_{cat}/K_m$) for chlorpyrifos methyl of at least about $3.5\times10^5$ $sec^{-1}\cdot M^{-1}$, for diazinon of at least about $3.6\times10^6$ $sec^{-1}\cdot M^{-1}$, for parathion ethyl of at least about $9\times10^7$ $sec^{-1}\cdot M^{-1}$, or a combination of two or more thereof, preferably all three.

In an embodiment, the polypeptide comprises at least three of a) to e). In another embodiment, the polypeptide comprises a) and c), and at least one of b), d) and e). In a further embodiment, the polypeptide comprises b), d) and e). In yet a further embodiment, the polypeptide comprises a) to e).

Preferably, the fragment of the invention comprises at least amino acids 20 to 296 of i) or ii), more preferably at least amino acids 15 to 325 of i) or ii), and even more preferably at least amino acids 10 to 350 of i) or ii).

Preferably, the polypeptide consists of the sequence of amino acids provided as SEQ ID NO:1.

In an embodiment, the polypeptide comprises the sequence of amino acids provided as SEQ ID NO:5.

In another embodiment, the polypeptide comprises or consists of the sequence of amino acids provided as SEQ ID NO:5.

In another aspect, the present invention provides a polypeptide which hydrolyses an organophosphate molecule and which has a second order rate constant ($k_{cat}/K_m$) for chlorpyrifos methyl of at least about $3.5\times10^5$ $sec^{-1}\cdot M^{-1}$, for diazinon of at least about $3.6\times10^6$ $sec^{-1}\cdot M^{-1}$, for parathion ethyl of at least about $9\times10^7$ $sec^{-1}\cdot M^{-1}$, or a combination of two or more thereof, preferably all three.

In an embodiment, a polypeptide of the invention is substantially purified and/or recombinant.

In an embodiment, a polypeptide, of the invention is a fusion protein further comprising at least one other polypeptide sequence. The at least one other polypeptide may be, for example, a polypeptide that enhances the stability of a polypeptide of the present invention, a polypeptide that promotes the secretion (such as a N-terminal hydrophobic signal peptide) of the fusion protein from a cell (such as a bacterial cell or a yeast cell), or a polypeptide that assists in the purification of the fusion protein (such as a maltose-binding protein or glutathione S-transferase).

In an embodiment, a polypeptide of the invention is immobilized on a solid support.

In a further embodiment, the polypeptide is present in a microbial cell or in an extract, preferably a crude extract, of a microbial cell.

In a further aspect, the present invention provides an isolated and/or exogenous polynucleotide comprising nucleotides whose sequence
  i) is set forth as SEQ ID NO:6,
  ii) encodes a polypeptide of the invention, or
  iii) is complementary along the full length of i) or ii).

In an embodiment, the polynucleotide is operably linked to a promoter capable of directing expression of the polynucleotide in a cell, preferably a microbial cell.

In a further aspect, provided is a vector comprising a polynucleotide of the invention.

In yet another aspect, provided is a host cell comprising a polynucleotide of the invention, and/or a vector of the invention. Examples of host cells of the invention include, but are not limited to, a plant cell or a microbial cell. Preferably, the microbial cell is a bacterial cell or a fungal cell such as a yeast cell. In one embodiment, the cell is suitable for fermentation.

In another aspect, the present invention provides a transgenic non-human organism comprising at least one cell of the invention.

In an embodiment, the transgenic non-human organism is a plant, a microbial organism, preferably a bacterium or a fungus.

In a further aspect, the present invention provides an extract of a host cell of the invention, and/or the organism of the invention, wherein the extract comprises a polypeptide of the invention, and optionally a polynucleotide of the invention.

In another aspect, the present invention provides a composition comprising one or more of a polypeptide of the invention, a polynucleotide of the invention, a vector of the invention, a host cell of the invention, and an extract of the invention, and one or more acceptable carriers.

In an embodiment, the composition comprises a cation such as, but not necessarily limited to, $Zn^{2+}$, $Fe^{2+}$, $Co^{2+}$, $Cd^{2+}$ or a combination of two or more thereof.

In yet another aspect, the present invention provides a method for hydrolysing an organophosphate molecule(s), the method comprising contacting the organophosphate molecule with one or more of a polypeptide of the invention, a host cell of the invention, an extract of the invention, and a composition of the invention.

In a preferred embodiment, the method of the above aspect comprises
a) obtaining a polypeptide of the invention, and
b) contacting the organophosphate molecule(s) with the polypeptide. In this embodiment, the polypeptide may form part of, for example, a host cell of the invention, an extract of the invention, or a composition of the invention.

In an embodiment, the organophosphate molecule is in or on the surface of a sample selected from the group consisting of: soil, water, biological material or a combination thereof.

In a further embodiment, the method comprises applying the one or more of the polypeptide, the polynucleotide, the vector, the host cell, the extract, and the composition to soil or a liquid, such a sheep dip, dam or tailwater, in the field.

In a further aspect, the present invention provides a method of treating toxicity caused by an organophosphate molecule in a subject, the method comprising administering to the subject one or more of a polypeptide of the invention, a host cell of the invention, an extract of the invention, or a composition of the invention.

Also provided is the use of one or more of a polypeptide of the invention, a polynucleotide of the invention, a vector of the invention, a host cell of the invention, an extract of the invention, and a composition of the invention for the manufacture of a medicament for treating toxicity caused by an organophosphate molecule in a subject.

Further, provided is the use of one or more of a polypeptide of the invention, a polynucleotide of the invention, a vector of the invention, a host cell of the invention, an extract of the invention, and a composition of the invention as a medicament for treating toxicity caused by an organophosphate molecule in a subject.

In a further aspect; the present invention provides a method of producing a polypeptide of the invention, the method comprising cultivating a host cell of the invention, or a vector of the invention, under conditions which allow expression of the polynucleotide encoding the polypeptide, and recovering the expressed polypeptide.

In a preferred embodiment, the method comprises
i) providing a vessel containing a liquid composition comprising cells of the invention suitable for fermentation, such as E. coli, and constituents required for fermentation, and
ii) providing conditions conducive to the fermentation of the liquid composition contained in said vessel.

In another aspect, the present invention provides a biosensor for detecting the presence of an organophosphate, the biosensor comprising a polypeptide of the invention, and a means for detecting hydrolysis of an organophosphate molecule by the polypeptide.

In a further aspect, the present invention provides a kit for hydrolysing an organophosphate molecule, the kit comprising one or more of a polypeptide of the invention, a host cell of the invention, an extract of the invention, and a composition of the invention.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. The chemical classes of organophosphate pesticides.

Figure 2:
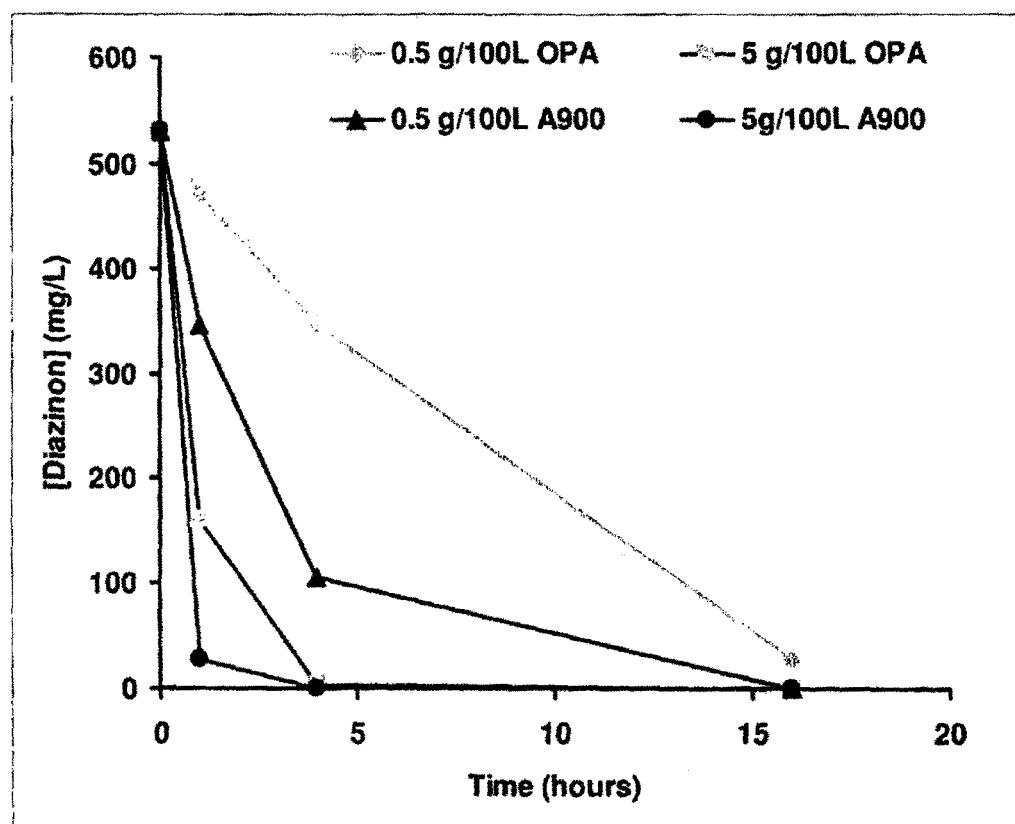

FIG. 2. Degradation of the organophosphorous insecticide diazinon by wild-type OpdA (OPA) and the improved variant (A900 comprising N-terminal Met).

Figure 3:
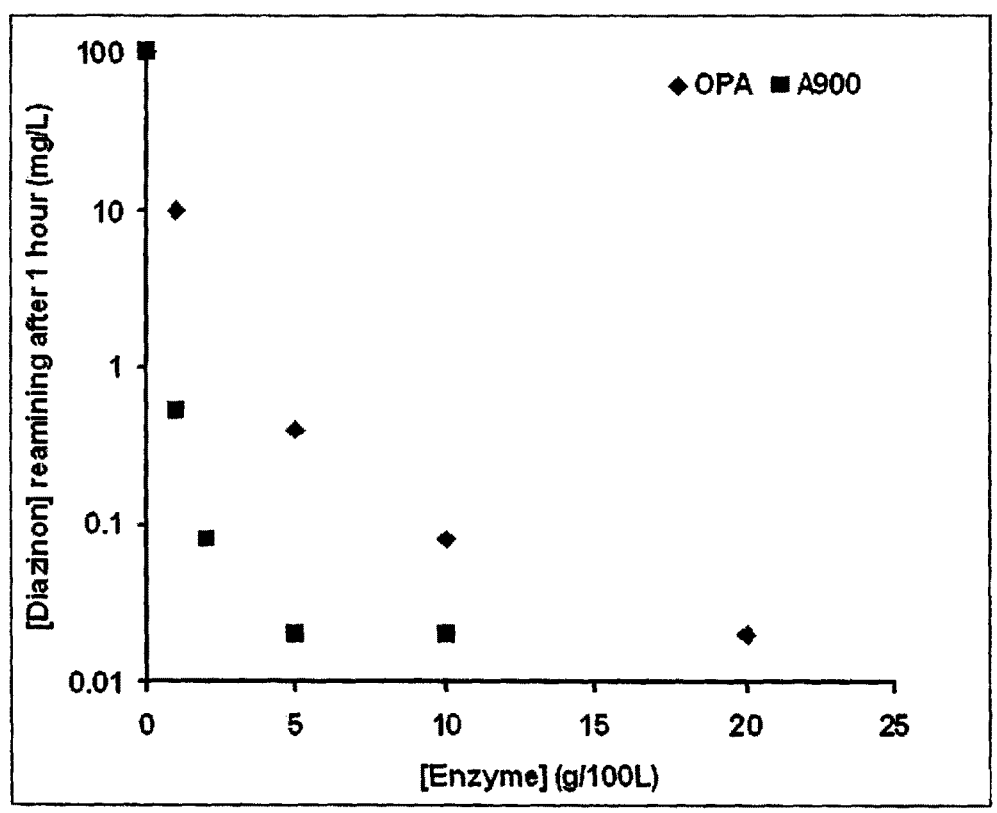

FIG. 3. Effect of dose rate of A900 (comprising N-terminal Met) and OpdA (OPA) on the extent of diazinon degradation in simulated sheep dip liquor after three hours.

Figure 4:
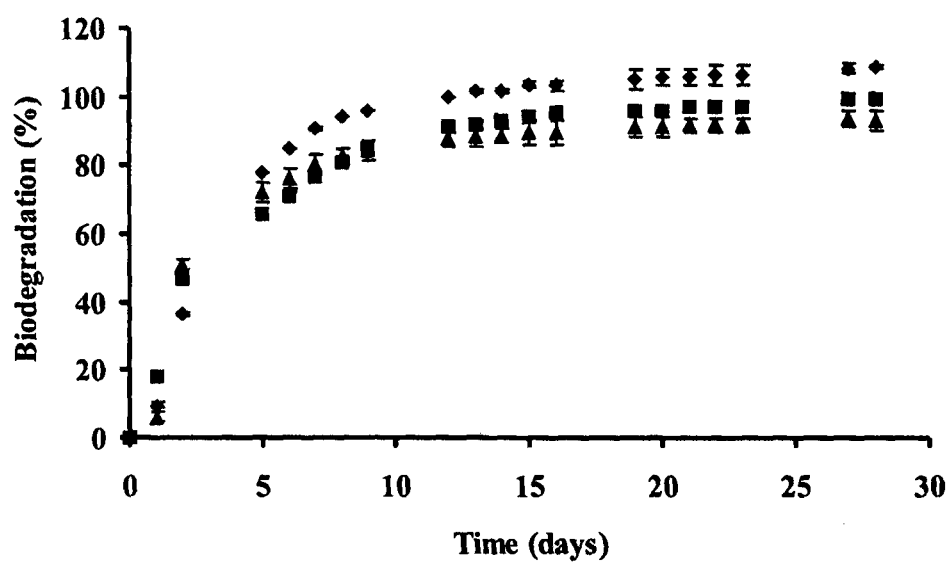

FIG. 4. Biodegradability of A900 (comprising N-terminal Met) (diamonds) and sodium benzoate (triangles) assessed by a manometric respirometry test. Inhibition of bacterial respiration by A900 was also assessed by measuring the rate of respiration in the presence of both sodium benzoate and A900 (squares).

KEY TO THE SEQUENCE LISTING

SEQ ID NO:1—Amino acid sequence of A900.
SEQ ID NO:2—Amino acid sequence of OpdA (native OpdA with the N-terminal 28 amino acids removed and an N-terminal Met added).
SEQ ID NO:3—Amino acid sequence of OpdA variant M4.
SEQ ID NO:4—Amino acid sequence of OPH.
SEQ ID NO:5—Amino acid sequence of A900 with an N-terminal Met added.
SEQ ID NO:6—Nucleotide sequence encoding A900.
SEQ ID NO:7—TAT-signal peptide.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, even more preferably +/−5%, of the designated value.

Throughout this specification the word "comprise", or variations, such as "comprises" or "comprising", will be understood to imply the inclusion of a stated element, integer or step, or group of elements, integers or steps, but not the exclusion of any other element, integer or step, or group of elements, integers or steps.

As used herein, the terms "hydrolyses", "hydrolysing", "hydrolysing activity" and variations thereof refer to the ability of a polypeptide of the invention to catalyze the hydrolysis of a chemical bond. In a preferred embodiment, the polypeptide "degrades" the organophosphate such that product of the activity of the enzyme is less toxic to, for example mammals and/or fish, and/or is less stable, than the organophosphate substrate.

As used herein, the term "greater organophosphate hydrolysing activity" refers to a polypeptide of the invention having a higher second order rate constant ($k_{cat}/K_m$) for an organophosphate when compared to a previously known polypeptide such as, but not limited to, a polypeptide whose amino acid sequence is set forth as SEQ ID NO:2, SEQ ID NO:3, or SEQ ID NO:4, preferably all three polypeptides. In a preferred embodiment, the term "greater organophosphate hydrolysing activity" refers to a polypeptide of the invention having one or more, preferably all three, of:

i) at least a 2 fold, or 4 fold or 6 fold higher second order rate constant ($k_{cat}/K_m$) for chlorpyrifos methyl than a polypeptide whose amino acid sequence is set forth as ID NO:2, SEQ ID NO:3, or SEQ ID NO:4, preferably all three, ii) at least a 1.5 fold or 2 fold higher second order rate constant ($k_{cat}/K_m$) for diazinon than a polypeptide whose amino acid sequence is set forth as SEQ ID NO:2, SEQ ID NO:3, or SEQ ID NO:4, preferably all three, and iii) at least a 2 fold, or 3 fold or 4 fold higher second order rate constant ($k_{cat}/K_m$) for parathion ethyl than a polypeptide whose amino acid sequence is set forth as SEQ ID NO:2, SEQ ID NO:3, or SEQ ID NO:4, preferably all three.

As used herein, the phrase "at a position corresponding to amino acid number" refers to the relative position of the amino acid compared to surrounding amino acids with reference to a defined amino acid sequence. For instance, in some embodiments a polypeptide of the invention may have additional N-terminal amino acids to assist with intracellular localization or extracellular secretion which alters the relative positioning of the amino acid when aligned against, for example, SEQ ID NO:1. In an example, upon performing a protein alignment the skilled person would readily comprehend that the proline at amino acid position 14 of SEQ ID NO:1 is the corresponding amino acid to the proline at amino acid position 15 of SEQ ID NO:1. In an embodiment, the polypeptide comprises the defined amino acid at the nominated residue number.

As used herein the terms "treating", "treat" or "treatment" include administering a therapeutically effective amount of, for example, a polypeptide of the invention, or a polynucleotide encoding therefor, sufficient to reduce or eliminate at least one symptom of toxicity caused by an organophosphate.

The term "biological material" is used herein in its broadest sense to include any product of biological origin. Such products include, but are not restricted to, food products for humans and animal feeds. The products include liquid media including water and liquid foodstuffs such as milk, as well as semi-solid foodstuffs such as yoghurt and the like. The present invention also extends to solid foodstuffs, particularly animal feeds. In an embodiment, it is preferred that the biological material is plant material such as, but not limited to, fruit, vegetables, sugar cane, canola seeds, wheat seeds, barley seeds, sorghum seeds, rice, corn, pineapples, or cotton seeds.

As used herein, the term "extract" refers to any portion of a host cell or non-human transgenic organism of the invention comprising a polypeptide of the invention, preferably also comprising a polynucleotide or vector of the invention. The portion may be a whole entity such as a seed, fruit, leaf, stem or root of a plant, or obtained by at least partial homogenization and/or purification. This term includes portions secreted from the host cell, and hence encompasses culture supernatants. Preferably the extract is a relatively crude extract which has not undergone a purification step to purify the polypeptide of the invention away from other polypeptides which were co-produced with the polypeptide of the invention. An extract may also be a composition comprising a polypeptide of the invention.

Organophosphates

Organophosphates are synthetic organophosphorus esters and related compounds such as phosphoroamidates. They have the general formula (RR'X)P=O or (RR'X)P=S, where R and R' are short-chain groups. R' in phosphoroamidates is a primary or secondary amine. For insecticidal organophosphates X is a good leaving group, which is a requirement for the irreversible inhibition of acetylcholinesterase.

The polypeptides of the present invention hydrolyse the phosphoester bonds of organophosphates. The organophosphate can have aromatic or aliphatic leaving groups (X) and can also contain vinyl groups (FIG. 1).

Preferably, the leaving group of the organophosphate has an ionisation constant (pKa) of less than 8 (Jackson et al., 2009).

Although well known for their use as pesticides, organophosphates have also been used as nerve gases against mammals. Accordingly, the polypeptides of the present invention are also useful for hydrolysis of organophosphates which are not pesticides. In a particularly preferred embodiment, the polypeptides of the invention are used to hydrolyse O-ethyl S-(2-diisopropyamino)ethyl methylpbosphonothiolate (VX).

Polypeptides

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, biologically active fragments, and/or modifications of the polypeptides described herein.

The % identity of a polypeptide is determined by GAP (Needleman and Wunsch, 1970) analysis (GCG program) with a gap creation penalty=5, and a gap extension penalty=0.3. The query sequence is at least 250 amino acids in length and the GAP analysis aligns the two sequences over a region of at least 250 amino acids. More preferably, the query sequence is at least 300 amino acids in length and the GAP analysis aligns the two sequences over a region of at least 300 amino acids. Even more preferably, the query sequence is at least 350 amino acids in length and the GAP analysis aligns the two sequences over a region of at least 350 amino acids. Even more preferably, the GAP analysis aligns the two sequences over their entire length.

As used herein a "biologically active fragment" is a portion of a polypeptide as described herein which maintains a defined activity of the full-length polypeptide. Biologically active fragments can be any size as long as they maintain the defined activity. Preferably; biologically active fragments are at least 300, more preferably at least 350, amino acids in length. Furthermore, biologically active fragment means a fragment with "organophosphate hydrolysing activity".

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

By "substantially purified" or "purified" we mean a polypeptide that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. Whilst at present there is no evidence that the polypeptides of the invention exist in nature, the terms native state and naturally associated also encompass the polypeptide produced in a host cell of the invention.

The term "recombinant" in the context of a polypeptide refers to the polypeptide when produced by a cell, or in a cell-free expression system, in an altered amount or at an altered rate compared to its native state. In one embodiment, the cell is a cell that does not naturally produce the polypeptide. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

Amino acid sequence mutants of a polypeptide described herein can be prepared by introducing appropriate nucleotide changes into a nucleic acid defined herein, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art, for example, using directed evolution or rational design strategies (see below). Products derived from mutated/altered DNA can readily be screened using techniques described herein to determine if they possess organophosphate hydrolysing activity (see, for instance, Examples 1 and 2). In another example, organophosphate hydrolysing activity is measured by dissolving the organophosphate in about 5% methanol and reacting the organophosphate with the enzyme in 50 mM Tris-HCl pH 8.0 at 25° C. Enzymatic activity is measured using standard procedures depending on the actual organophosphate. For example, chlorpyrifos can be measured spectrophotometrically by monitoring the increase in absorbance at 276 nm (Dumas et al., 1989b), whereas the hydrolysis of diazinon can be monitored using radiolabelled diazinon (ethyl-1-$^{14}$C; 14.8 MBq/mmol) in the radiometric partition assay previously used for radiolabelled OP substrates (Campbell et al., 1998).

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Sites of interest are those in which particular residues obtained from various strains or species are identical. These positions may be important for biological activity. These sites, especially those falling within a sequence of at least three other identically conserved sites, are preferably substituted in a relatively conservative manner. Examples of conservative substitutions are shown in Table 1.

In a preferred embodiment, a mutant/variant polypeptide has only conservative substitutions when compared to a polypeptide specifically defined herein.

In a preferred embodiment a mutant/variant polypeptide has one or two or three or four conservative amino acid changes when compared to a polypeptide specifically defined herein. Details of conservative amino acid changes are provided in Table 1. Preferably, if not specified otherwise, at a given amino acid position the polypeptide comprises an amino acid as found at the corresponding position of the polypeptide provided as SEQ ID NO:1.

Guidance regarding further substitution mutations which can be made is described in Yang et al. (2003), Cho et al. (2004), Horne et al. (2006) and Jackson et al. (2009).

If an amino acid at a nominated site is inconsistent with an amino acid substitution provided in Table 1, the nominated amino acid is preferred.

TABLE 1

Exemplary substitutions.

| Original Residue | Exemplary Substitutions |
|---|---|
| Ala (A) | val; leu; ile; gly; ser |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr; ala |
| Thr (T) | ser |
| Trp (W) | tyr |
| Tyr (Y) | trp; phe |
| Val (V) | ile; leu; met; phe; ala |

In a preferred embodiment, a polypeptide of the invention comprises one or more, preferably all, of the following;

i) a histidine at a position corresponding to amino acid number 26 of SEQ ID NO:1, ii) a histidine at a position corresponding to amino acid number 28 of SEQ ID NO:1, iii) a lysine at a position corresponding to amino acid number 140 of SEQ ID NO:1, iv) a histidine at a position corresponding to amino acid number 172 of SEQ ID NO:1, v) a histidine at a position corresponding to amino acid number 201 of SEQ ID NO:1, vi) an arginine at a position corresponding to amino acid number 225 of SEQ ID NO:1, vi) a tyrosine at a position corresponding to amino acid number 228 of SEQ ID NO:1, and vii) an aspartic acid at a position corresponding to amino acid number 272 of SEQ ID NO:1.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide. Preferably, a lysine at a position corresponding to amino acid number 140 of SEQ ID NO:1 is present, and the lysine is carbamylated.

Polypeptides described herein can be produced in a variety of ways, including production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

In an embodiment, a polypeptide of the invention comprises a signal sequence which is capable of directing secretion of the polypeptide from a cell. As the skilled person would appreciate, the signal sequence may or not be cleaved, or be partially cleaved, whilst being partially exported from the cell. However, when removing a signal sequence the cell may produce a heterogeneous population of polypeptides with slightly different, for example, N-terminal sequences. Thus, the term "consists of" encompasses such variants produced by the removal of signal sequences. A large number of such signal sequences have been isolated, which include N- and C-terminal signal sequences. Prokaryotic and eukaryotic N-terminal signal sequences are similar, and it has been shown that eukaryotic N-terminal signal sequences are capable of functioning as secretion sequences in bacteria. An example of such an N-terminal signal sequence is the bacterial β-lactamase signal sequence, which is a well-studied sequence, and has been widely used to facilitate the secretion of polypeptides into the external environment. An example of C-terminal-signal sequences is the hemolysin A (hlyA) signal sequences of E. coli. Additional examples of signal sequences include, without limitation, aerolysin, alkaline phosphatase gene (phoA), chitinase, endochitinase, α-hemolysin, MIpB, pullulanase, Yops and a TAT signal peptide.

In one embodiment, the signal sequence is the TAT signal peptide (MSLSRRQFIQASGIALCAGAVPLKASA (SEQ ID NO:7)), where most, if not all, of the signal sequence is not cleaved when the polypeptide recombinantly expressed and secreted. In this embodiment, a polypeptide of the invention consists of SEQ ID NO:1 with SEQ ID NO:7 at the N-terminus.

Directed Evolution

In directed evolution, random mutagenesis is applied to a protein, and a selection regime is used to pick out variants that have the desired qualities, for example, increased organophosphate hydrolysing activity. Further rounds of mutation and selection are then applied. A typical directed evolution strategy involves three steps:

1) Diversification: The gene encoding the protein of interest is mutated and/or recombined at random to create a large library of gene variants. Variant gene libraries can be constructed through error prone PCR (see, for example, Leung, 1989; Cadwell and Joyce, 1992), from pools of DNaseI digested fragments prepared from parental templates (Stemmer, 1994a; Stemmer, 1994b; Crameri et al., 1998; Coco et al, 2001) from degenerate oligonucleotides (Ness et al., 2002, Coco, 2002) or from mixtures of both, or even from undigested parental templates (Zhao et al., 1998; Eggert et al., 2005; Jézéquek et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the E. coli XL-1 red (Stratagene) and propagating the transformed bacteria for a suitable number of, generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection: The library is tested for the presence of mutants (variants) possessing the desired property using a screen or selection. Screens enable the identification and isolation of high-performing mutants by hand, while selections automatically eliminate all nonfunctional mutants. A screen may involve expressing the mutated polynucleotide in a host organsim or part thereof and assaying the level of organophosphate hydrolysing activity.

3) Amplification: The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

The rational design of further variants can be facilitated by the available information regarding the structure/function relationship of OPD-related enzymes such as described in Jackson et al. (2009) and Wu et al. (2000). Such studies have shown the importance of maintain certain amino acids for function such as the histidine at a position corresponding to amino acid number 26 of SEQ ID NO:1, the histidine at a position corresponding to amino acid number 28 of SEQ ID NO:1, the lysine at a position corresponding to amino acid number 140 of SEQ ID NO:1, the histidine at a position corresponding to amino acid number 172 of SEQ ID NO:1, the histidine at a position corresponding to amino acid number 201 of SEQ ID NO:1, the arginine at a position corresponding to amino acid number 225 of SEQ ID NO:1, the tyrosine at a position corresponding to amino acid number 228 of SEQ ID NO:1, and the aspartic acid at a position corresponding to amino acid number 272 of SEQ ID NO:1.

Polynucleotides

As used herein, an "isolated polynucleotide" means a polynucleotide which is at least partially separated from the polynucleotide sequences with which it is associated or linked in its native state. Isolated polynucleotides include DNA and RNA molecules, and molecules that are a combination of DNA and RNA. They may be single-stranded, double stranded or partially double-stranded, and may be in a sense or antisense orientation with respect to a promoter. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polynucleotides of the present invention may possess, when compared to molecules provided herewith, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Usually, monomers of a polynucleotide are linked by phosphodiester bonds or analogs thereof. Analogs of phosphodiester linkages include: phosphorothioate, phosphorodithioate, phosphoroselenoate, phosphorodiselenoate, phosphoroanilothioate, phosphoranilidate and phosphoramidate.

Recombinant Vectors

One embodiment of the present invention includes a recombinant vector, which comprises at least one isolated/exogenous polynucleotide of the invention inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises the polynucleotide(s) operably linked to an expression vector. The phrase operably linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors include any vectors that function (i.e., direct gene expression) in recombinant cells, including in bacterial, fungal, endoparasite, arthropod, animal, and plant cells. Vectors of the invention can also be used to produce the polypeptide in a cell-free expression system, such systems are well known in the art.

"Operably linked" as used herein refers to a functional relationship between two or more nucleic acid (e.g., DNA) segments. Typically, it refers to the functional relationship of transcriptional regulatory element to a transcribed sequence. For example, a promoter is operably linked to a coding sequence, such as a polynucleotide defined herein, if it stimulates or modulates the transcription of the coding sequence in an appropriate host cell and/or in a cell-free expression system. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, nematode, plant or animal cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Host Cells

Another embodiment of the present invention includes a host cell transformed with one or more recombinant molecules described herein or progeny cells thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides described herein or can be capable of producing such polypeptides after being transformed with at least one polynucleotide molecule as described herein. Host cells of the present invention can be any cell capable of producing at least one protein defined herein, and include bacterial, fungal (including yeast), parasite, nematode, arthropod, animal and plant cells. Examples of host cells include *Salmonella, Escherichia, Bacillus, Listeria, Saccharomyces, Spodoptera*, Mycobacteria, *Trichoplusia*, BHK (baby hamster kidney) cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Useful yeast cells include *Pichia* sp., *Aspergillus* sp. and *Saccharomyces* sp. Particularly preferred host cells are bacterial cells, fungal cells or plant cells.

In one embodiment, the cell is suitable for fermentation. Examples of useful bacterial cell for fermentation include, but are not limited to, *Escherichia* sp. (such as *Escherichia coli*), *Bacillus* sp. (such as *Bacillus subtilis* and *Bacillus licheniformis*), *Lactobacillus* sp. (such as *Lactobacillus brevis*), *Pseudomonas* sp. (such as *Pseudomonas aeruginosa*) and *Streptomyces* sp. (*Streptomyces lividans*). Examples of useful fungal cells for fermentation include, but are not limited to, *Candida* sp. (such as *Candida albicans*), *Hansenula* sp. (such as *Hansenula polymorpha*), *Pichia* sp. (*Pichia pastoris*), *Kluveromyces* sp. (such as *Kluyveromyces marxianus*), and *Saccharomyces* sp. (*Saccharomyces cerevisiae*).

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Transgenic Plants

The term "plant" as used herein as a noun refers to a whole plants such as, for example, a plant growing in a field for commercial plant or grain production. A "plant part" refers to vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant" refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Plants contemplated for use in the practice of the present invention include both monocotyledons and dicotyledons. Target plants include, but are not limited to, the following: cereals (for example, wheat, barley, rye, oats, rice, maize, sorghum and related crops); beet (sugar beet and fodder beet); pomes, stone fruit and soft fruit (apples, pears, plums, peaches, almonds, cherries, strawberries; raspberries and black-berries); leguminous plants (beans, lentils, peas, soybeans); oil plants (peanut, rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, vines, hops, turf, bananas and natural rubber plants, as well as ornamentals (flowers, shrubs, broad-leaved trees and evergreens, such as conifers). Crops frequently effected by *Aspergillus* sp. infection which are target plants of the invention include, but are not limited to, cereals (maize, sorghum, pearl millet, rice, wheat), oilseeds (peanut, soybean, sunflower, cotton), spices (chile peppers, black pepper, coriander, turmeric, ginger), and tree nuts (almond, pistachio, walnut, coconut). In a preferred embodiment, the plant is selected from sugar, cotton, corn, sorghum, pineapple, conifers such as christmas trees, eucalypts, wheat, oats, barley, rice and canola.

A polynucleotide of the present invention may be expressed constitutively in the transgenic plants during all stages of development. Depending on the use of the plant or plant organs, the polypeptides may be expressed in a stage-specific manner. Furthermore, the polynucleotides may be expressed tissue-specifically.

Regulatory sequences which are known or are found to cause expression of a gene encoding a polypeptide of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α,β binding protein gene promoter. These promoters have been used to create DNA vectors that have been expressed in plants; see, e.g., WO 84/02913. All of these promoters have been used to create various types of plant-expressible recombinant DNA vectors.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase promoter from wheat, the nuclear photosynthetic ST-LS 1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-H$^{30}$ symporter promoter, and the promoter for the thylakoid membrane protein genes from spinach (PsaD, PsaF, PsaE, PC, FNR, AtpC, AtpD, Cab, RbcS).

For the purpose of expression in sink tissues of the plant, such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter, the promoter for the potato tuber ADPGPP genes, both the large and small subunits, the sucrose synthase promoter, the promoter for the major tuber proteins including the 22 kD protein complexes and proteinase inhibitors, the promoter for the granule bound starch synthase gene (GBSS), and other class I and II patatins promoters. Other promoters can also be used to express a protein in specific tissues, such as seeds or fruits. The promoter for β-conglycinin or other seed-specific promoters such as the napin and phaseolin promoters, can be used. A particularly preferred promoter for *Zea mays* endosperm expression is the promoter for the glutelin gene from rice, more particularly the Osgt-1 promoter.

Root specific promoters may also be used. An example of such a promoter is the promoter for the acid chitinase gene. Expression in root tissue could also be accomplished by utilizing the root specific subdomains of the CaMV 35S promoter that have been identified.

The 5' non-translated leader sequence can be derived from the promoter selected to express the heterologous gene sequence of the polynucleotide of the present invention, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) are coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun, available from Bio-Rad Laboratories.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310 5,004,863, 5,159,135). Further, the integration of the T-DNA is a relatively precise process resulting in few rearrangements. The region of DNA to be transferred is defined by the border sequences, and intervening DNA is usually inserted into the plant genome.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Compositions

Compositions of the present invention include excipients, also referred to herein as "acceptable carriers". An excipient can be any material that the animal, plant, plant or animal material, or environment (including soil and water samples) to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal or o-cresol, formalin and benzyl alcohol. Excipients can also be used to increase the half-life of a composition, for example; but are not limited to, polymeric controlled release vehicles, biodegradable implants, liposomes, bacteria, viruses, other cells, oils, esters, and glycols.

In an embodiment, a polypeptide of the invention is immobilized on a solid support. This can enhance the rate and/or degree of hydrolysis of an organophosphate and/or increase the stability of the polypeptide. For example, the polypeptide can be immobilized on a polyurethane matrix (Gordon et al., 1999), or encapsulated in appropriate liposomes (Petrikovics et al., 2000a and b). The polypeptide can also be incorporated into a composition comprising a foam such as those used routinely in fire-fighting (LeJeune et al., 1998). As would be appreciated by the skilled addressee, the polypeptide of the present invention could readily be used in a sponge or foam as disclosed in WO 00/64539. Other solid supports useful for the invention include resins with an acrylic type structure, with epoxy functional groups, such as Sepabeads EC-EP (Resindion srl—Mitsubishi Chemical Corporation) and Eupergit C (Rohm-Degussa), or with primary amino groups, such as Sepabeads EC-has and EC-EA (Resindion srl—Mitsubishi Chemical Corporation). In any case, the polypeptide is brought in contact with the resin and immobilized through the high reactivity of the functional groups (epoxides) or activation of the resin with a bifunctional agent, such as glutaraldehyde, so as to bind the enzyme to the matrix. Other resins suitable for the invention are polystyrene resins, macroreticular resins and resins with basic functional groups, such as Sepabeads EC-Q1A: the polypeptide is absorbed on the resin and then stabilized by cross-linking with a bifunctional agent (glutaraldehyde).

Enzymes of the invention require a cation for activity. Thus, if the sample to be treated does not have sufficient levels of cations they may need to be added. Examples of suitable cations include, but not necessarily limited to, $Zn^{2+}$, $Fe^{2+}$, $CO^{2+}$, $Cd^{2+}$ or a combination of two or more thereof.

One embodiment of the present invention is a controlled release formulation that is capable of slowly releasing a composition of the present invention into an animal, plant, animal or plant material, or the environment (including soil and water samples). As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Preferred controlled release formulations are biodegradable (i.e., bioerodible). Slow release compositions are particulaiiy useful for use in moving water.

A preferred controlled release formulation of the present invention is capable of releasing a composition of the present invention into soil or water which is in an area comprising an organophosphate. The formulation is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

In an alternate embodiment, the composition is a dried composition. More preferably, a dried extract of a cell, such as bacterial cell, expressing a polypeptide of the invention. Preferably the cell extract is partially purified before drying, for instance as described in Example 1. A liquid composition can be dried using any technique known in the art such as, but not limited to, freeze drying, spray drying and drum drying. The dried composition can be used as an additive to a liquid comprising an organophosphate to be at least partially decontaminated such as a dam, municiple waste water, an animal dip, a produce (such as vegetables or fruit) dip, or cleaning fluid for use on machinery/equipment.

Wastewater can treated using a polypeptide of the invention in one or more wastewater treatment units, which may include methods such as screening, sedimentation, activated sludge, surface-aerated basins, filter beds, oxidizing beds, biological aerated filters, membrane bioreactors, rotating biological contactors, filtration, lagooning, nutrient removal, nitrogen removal, phosphorus removal, disinfection, and the like. In one embodiment, a polypeptide of the invention is immobilized in a filter bed.

The concentration of the polypeptide, vector, or host cell etc of the present invention that will be required to produce effective compositions for hydrolysing an organophosphate, will depend on the nature of the sample to be decontaminated, the concentration of the organophosphate in the sample, and the formulation of the composition. The effective concentration of the polypeptide, vector, or host cell etc within the composition can readily be determined experimentally using a method of the invention. In a preferred embodiment, about 6 to 20 g/L, more preferably about 8 to 15 g/L, and even more preferably about 10 g/L of the polypeptide is used.

Enzymes of the invention, and/or host cells encoding therefor, can be used in coating compositions as generally described in WO 2004/112482 and WO 2005/26269.

Biosensors

Biosensors are analytical devices typically consisting of a biologically active material such as an enzyme and a transducer that converts a biochemical reaction into a quantifiable electronic signal that can be processed, transmitted, and measured. A general review of biosensors which have been used for the detection of orangophosphorus compounds is provided by Rekha et al. (2000). The polypeptide of the present invention can readily be adapted for use in such biosensors.

EXAMPLES

Example 1

OpdA Variant A900 has Enhanced Activity when Compared to OpdA

Enzyme Production

A plasmid was constructed including a coding region having the nucleotide sequence of SEQ ID NO: 6 that encoded the amino acid sequence of SEQ ID NO: 1. A stock E. coli BL21 (DE3) culture in glycerol was removed and transformed with plasmid DNA encoding the enzyme. A few colonies of E. coli were scraped from the transfer plate and dipped into nutrient media and incubated at 37° C. (Primary seed). At a certain cell concentration a small amount was added to flasks containing 500 mL of media. The secondary seeds were similarly incubated and at a certain cell concentration were pooled and used as inoculum for the fermenter (1,000 L).

A 1,000 L fermenter was charged with nutrient medium (600 L) of defined composition followed by sterilisation at 121° C. for 1 hour. Following sterilisation the medium was adjusted to pH 7 and inoculum added so as to initiate fermentation. The conditions of temperature, pH, dissolved oxygen (airflow and agitation), and carbohydrate addition were controlled so as to facilitate conversion of media components into useful biomass.

Harvest culture was diluted to 2000 L. A continuous homogeniser was used to break up cells and release enzyme into the liquid. The homogenate was centrifuged to remove cell debris and supernatant is collected in a tank. This was performed in a continuous centrifuge. Clarified supernatant was pumped out of the tank, through a filtration train and into a tank. The train consisted of three depth filters and a Milligard filter of 0.65 μm nominal rating. The total volume at this stage was 2,000 L.

Using 30 kD molecular cut-off membrane, the product was concentrated to 150 L. To ensure a GMO free product, the concentrated product was filtered through an 0.2 μM absolute filter. The final filtered product was collected in a 200 L vessel and freeze dried. In a second fermentation, the same procedure was used to produce an OpdA polypeptide (WO2002/92803). Approximately 20 kg (OpdA) and 25 kg (A900) freeze dried mass were produced per batch.

Enzyme Activity

Sheep Dip

The efficacy of a variant of the organophosphate hydrolase (A900) (SEQ ID NO:1) was compared with its parent (OpdA; OPA) (SEQ ID NO:2) by testing in simulated sheep dip liquor. Two experiments were conducted. A simulated sheep dip solution was prepared using tap water, 9 g/L sheep droppings and 14 g/L alkaline clay soil. The diazinon containing formulation was added to the water first and then the solids were introduced which is the order in which it occurs in the field. The limit of detection in the experiments was <0.05 mg/L.

The first experiment (FIG. 2) measured the degradation of diazinon in the simulated dip liquor over a period of 16 hours at two dose rates of OPA and A900 (0.5 g/100 L and 5 g/100 L). The initial diazinon concentration in the simulated liquor was 530 mg/L.

At the low dose rate the wild-type OpdA had hydrolysed 11%, 35% and 94.7% after 1, 4 and 16 hours respectively, whilst the A900 variant had hydrolysed 35%, 80% and 99.96% over the same time periods. As 35% hydrolysis was achieved by the wild-type in 4 hours at the lower dose rate and the variant in 1 hour at the same dose rate it suggests that the variant hydrolyses diazinon at least 4-fold faster than the wild-type.

At the higher dose rate (5 g/100 L) the wild-type enzyme had hydrolysed 70%, 99.3% and 99.6% after 1, 4 and 16 hours respectively. The A900 variant hydrolysed 95%, 99.9% and 99.99% after 1, 4 and 16 hours respectively. This result confirms that the A900 variant has a superior rate of diazinon hydrolysis that the wild-type enzyme.

In the second experiment the dose rates of A900 and wild-type enzyme were varied and the extent of diazinon degradation assessed after 3 hours incubation (FIG. 3). The initial diazinon concentration was 100 mg/L. At the lowest dose rate (1 g/IDOL) wild-type OpdA degraded 90% of the diazinon in the sample, whilst the A900 variant degraded >99% of the diazinon, consistent with an enhanced rate of hydrolysis by the variant enzyme. As the dose rate increased the variant enzyme maintained a log greater rate of hydrolysis than the wild-type confirming the enhanced rate of degradation compared with the wild-type.

Tail Water Treatment

OP insecticides are also widely used to reduce pest damage in agricultural and horticultural crops. In the case of irrigated cropping a significant proportion of the OP contaminant is often washed into drainage or interception ditches along with irrigation tail water, from where a variety of secondary contamination scenarios may ensue.

The first field trial treating OP-contaminated tail water with OpdA was reported in 2001, with a >90% reduction in OP concentration achieved in just 10 minutes (Russell et al., 2001). In this early trial, and also in subsequent ones, a concentrated solution of OpdA was 'bled' into the flowing tail water as it entered the drainage ditch at a rate that determined the final U/L dose rate. In the field trial conducted at Coleambally, NSW (2007), tail water contaminated with 55 mg/L chlorpyrifos was treated with 7, 35 or 70 U/L OpdA. All three dosing regimes achieved >99% 35 degradation of the OP, in 2 hours at the lowest dose rate and in less than 15 minutes at the highest dose rate.

In Gustine (California), a lower dose rate (0.59 U/L) was used to treat low level chlorpyrifos contamination (2.24 mg/L) in tail water from an alfalfa crop. Even with this low dose rate, 93% degradation of the chlorpyrifos was achieved in just 3 hours. The treatment of tail water is tightly time-bound (because it is generally necessary in these circumstances to achieve substantive detoxification before the water in question leaves the farm and joins public waterways) and the dose rate of OpdA cannot be reduced by allowing a longer reaction time. From the field trial data, a dose rate of between 0.59 and 7 U/L appears to be required to achieve greater than 99% degradation of chlorpyrifos in less than two hours.

These field trials demonstrate that significant tail water decontamination can be achieved using OpdA. Similarly, the use of A900 will also produce significant tail water decontamination.

Soil Treatment

The treatment of crops with OPs can also contaminate soil, which can lead to the contamination of ground water. Therefore, a potential application of free enzyme bioremediation is in treating contaminated soils.

Trials with OpdA in soil treatment have been conducted in Australia (Nagambie, Victoria). Almond trees were treated with diazinon (Country Diazinon; 500 g/L) at a rate of 2 L/ha, resulting in an average diazinon concentration of 6.4 mg/kg in the first 1 cm depth of top soil. OpdA was applied at 250, 500, or 1000 g/ha (in a water volume of 1000 L/ha) 1 hour after pesticide application. In samples taken at 1 hour after OpdA application a 39% (250 g/ha), 61% (500 g/ha) and 77% (1000 g/ha) reduction in diazinon was observed. Similarly, the use of A900 produces significant soil OP decontamination. The inclusion of surfactants in the formulation is expected to permit greater OP degradation in soils.

Commodity Treatment

Post-harvest contamination of commodities is also a concern. Many governments impose strict Maximum Residue Limits (MRLs) on both domestic and imported commodities. These restrictions can constitute significant constraints on commodity trading, with serious economic impacts on growers. Post-harvest treatment of commodities with a bioremediant could help reduce contamination.

Trials of OpdA have been conducted with eggplant, tomato and mango treated with fenitrothion, diazinon, chlorpyrifos and phenthoate. Reductions of up to 40% in chlorpyrifos levels and 35% in diazinon concentrations were obtained in eggplant after 5 minutes treatment. Residues of fenitrothion on eggplant and tomato were reduced by 53% and 12%, respectively, and phenthoate residues on eggplant and tomato were reduced by 66% and 53%, respectively, after 15 minutes treatment. Phenthoate and diazinon residues were reduced by 21% and 24% respectively in mango peel. Similarly, A900 is useful in reducing OP contamination of commodities.

Example 2

Improved Steady State Kinetics of A900 Compared with OpdA, OPH and the Best Methyl Paraoxon Degrading OpdA Variant in the Literature (M4)

$k_{cat}/K_M$ values were obtained for enzymes (OPH, OpdA, OpdA900 (SEQ ID NO:1 further comprising an N-terminal Met) and OpdA M4) purified by the methods described in Jackson et al. (2006). OPH is an alternative organophosphate hydrolase from *Pseudomomas dimuta* (Dumas et al., 1989b), OpdA900 and OpdA M4 are variants of OpdA. M4 was the variant of OpdA that had the greatest reported activity as tested against the OP insecticide methyl paraoxon (Jackson et al., 2009). M4 was 98.8% identical to the wild-type OpdA, A900 was 98.5% identical to wild-type OpdA, and M4 was 98.8% identical to A900 (Table 2).

TABLE 2

Percent identity of the OpdA variants investigated in this study.

| Sequence | OpdA | M4 | A900 |
|---|---|---|---|
| OpdA | 100.0 | 98.8 | 98.5 |
| M4 | 98.8 | 100.0 | 98.5 |
| A900 | 98.5 | 98.5 | 100.0 |

Protein concentrations were measured by UV absorption at 280 nm using a Nanodrop ND 1000 spectrophotometer (ThermoFisher Scientific), using a molar extinction coefficient of 29,280 $M^{-1} \cdot cm^{-1}$ (Jackson et al., 2006).

Hydrolysis rates were determined at 25° C. in MOPS buffer (pH8.0) comprising 100 mM $CoCl_2$ using UV-vis spectroscopy at 250 nm (diazinon), 330 nm (chlorpyrifos ethyl and methyl) and 405 nm (parathion ethyl and methyl). The formation of product was monitored using a SpectraMax M5 spectrophotometer (Molecular Devices). Rates of hydrolysis were obtained for 5, 10, 25, 50, 75, 100 and 200 µM concentrations of each substrate for each enzyme, and their $K_M$ and $V_{max}$ values derived using the Lineweaver-Burke method. The enzymes' $k_{cat}$ values were determined by dividing the $V_{max}$ values by the enzyme concentration in the assays (Table 3).

TABLE 3

Steady state kinetics for OPH, OpdA, A900 and M4 for industrially relevant OP insecticides. The highest $k_{cat}/K_M$ value for each insecticide is underlined.

| | OPH | | | OpdA | | | A900 | | | M4 | | |
|---|---|---|---|---|---|---|---|---|---|---|---|---|
| Insecticide | $k_{cat}$ | $K_M$ | $k_{cat}/K_M$ | $k_{cat}$ | $K_M$ | $k_{cat}/K_M$ | $k_{cat}$ | $K_M$ | $k_{cat}/K_M$ | $k_{cat}$ | $K_M$ | $k_{cat}/K_M$ |
| Chlorpyrifos ethyl | 22 | 43 | $5.14 \times 10^5$ | 171 | 61 | $2.82 \times 10^6$ | 308 | 143 | $2.15 \times 10^6$ | 40 | 133 | $3.30 \times 10^5$ |
| Chlorpyrifos methyl | 10 | 382 | $2.70 \times 10^4$ | 9 | 443 | $1.95 \times 10^4$ | 29 | 79 | $3.65 \times 10^5$ | 11 | 194 | $5.61 \times 10^4$ |
| Diazinon | 6 | 13 | $4.59 \times 10^5$ | 136 | 72 | $1.89 \times 10^6$ | 1095 | 283 | $3.87 \times 10^6$ | 30 | 270 | $1.09 \times 10^5$ |
| Parathion ethyl | 2354 | 241 | $9.77 \times 10^6$ | 652 | 38 | $1.70 \times 10^7$ | 7822 | 82 | $9.54 \times 10^7$ | 697 | 32 | $2.18 \times 10^7$ |
| Parathion methyl | 32 | 285 | $1.11 \times 10^5$ | 1039 | 208 | $4.99 \times 10^6$ | 1038 | 289 | $3.59 \times 10^6$ | 1094 | 287 | $3.87 \times 10^6$ |

$k_{cat}$, catalytic constant (sec−1);
$K_M$, Michaelis constant (µM);
$k_{cat}/K_M$, second order rate constant (sec−1 · M−1).

TABLE 4

Ecotoxicity and mammalian toxicity of OpdA.

| Test | Monitoring time | Dose rate | Effect of OpdA |
|---|---|---|---|
| Scenedesmus subspicatus | 72 hour | 100 mg/L | No growth effects observed |
| Activated sludge | 3 hour | 1000 mg/L | No inhibitory effect on bacterial respiration |
| Brachydanio rerio | 96 hour | 100 mg/L | No mortality or visible abnormalities observed |
| Daphnia magna | 48 hour | 100 mg/L | No mortality (immobilisation of cells) observed |
| Wistar rat (oral) (n = 30, 15 male and 15 female at each dose rate) | 28 day | 50, 200 and 1000 mg/kg/day | All test animals survived with no apparent signs of toxicity. No adverse responses were observed. |
| Rats (Dermal) (n = 10, 5 male and 5 female) | 15 days | 4 mL/kg of a 0.5 g/mL solution | Slight general erythema observed in test animals. No clinical effects noted. |

A 900 had the highest second order rate constants of the enzymes tested against diazinon, methyl chlorpyrifos and ethyl parathion, whilst maintaining 76.2% of the activity of the fastest enzyme against ethyl chlorpyrifos and 71.9% of the activity of the fastest enzyme against methyl parathion.

Example 3

Toxicity of OpdA and the OP Metabolites

Toxicity of OpdA

The toxicity of OpdA to mammals was established in formal toxicity studies with Wistar rats (Table 4). OpdA was either fed or applied dermally to the animals (Table 4) at dose rates of 50, 200 and 1000 mg/kg per day for 28 days (oral) or at 4 mL/kg of a 500 mg/mL solution per day for 15 days (dermal). Biopsies revealed no noticeable detrimental effects of oral OpdA application in the rats, whilst the dermal application produced a mild skin irritation with no clinical effects.

The environmental toxicity of OpdA was tested by applying it at 1 g/L to activated sludge, and at 100 mg/L to cultures of the alga Scenedesmus subspicatus, the arthropod Daphnia magna, and the fish species Brachydanio rerio, with no adverse affects found in any of these indicator species (Table 4). The dose rates used in these toxicity and ecotoxicity studies were higher than in many of the successful field trials of the enzyme's efficacy as a bioremedian, demonstrating that it can be used in environmental applications without adverse environmental effects.

The ecotoxicology studies of OpdA were also complemented with a study of its biodegradability (FIG. 4). In this study the rate of digestion of OpdA was assessed in a manometric respirometry test, whereby the amount of OpdA digested was calculated based on the biological oxygen demand of activated sludge fed with OpdA as a carbon source. An equivalent amount of carbon, provided as the readily digestible compound sodium benzoate, was used as a positive control. The result of this test was that >95% of both the OpdA and the sodium benzoate were digested over a 15 day period, showing that OpdA was readily degraded. Furthermore, there was no reduction in the biological oxygen demand when sodium benzoate and OpdA were added simultaneously, suggesting that OpdA has no inhibitory affect upon bacterial growth when it was not the sole carbon source. The stability of OpdA in natural water was also monitored, using the hydrolysis of methyl parathion as an indication of the relative amount of remaining in the sample (Table 5). In this experiment the half-life of OpdA was seventy nine hours, with less than 1 percent of the original activity remaining after seven days. These data suggested that OpdA was biodegradable, and has a relatively short half-life in natural systems. Experiments with A900 indicate that it is as biodegradable as OpdA.

TABLE 5

Stability of OpdA in natural water.

| Time (hours) | Activity (U/L)* | Activity (% initial) |
|---|---|---|
| 0 | 2133 | 100% |
| 17 | 2306 | 108% |
| 24 | 2341 | 110% |
| 48 | 1894 | 89% |
| 96 | 624.4 | 29% |
| 168 | 19.55 | 0.92% |

*The activity (U/L) of OpdA was measured using methyl parathion as substrate. One unit of enzyme activity (U) is equivalent to the amount of enzyme required to hydrolyse 1 μmol of methyl parathion per minute. The values shown are the mean of two replicate that did not differed by less than 5% at each reading.

Metabolite Toxicity

Detoxification of the pesticide was established by exposing an indicator arthropod species, Ceriodaphnia dubia, to either untreated diazinon (50 mg/L) or diazinon (50 mg/L) that had been pre-treated with OpdA (Table 6). The survival rate of the Ceriodaphnia was monitored after 24 and 48 hours of exposure. At both time points the $EC_{50}$ (effective concentration for 50% survival) for Ceriodaphnia exposed to the OpdA treated diazinon was nearly 200,000 times greater than for exposure to the untreated pesticide. Similar increases in the LOEC (Lowest concentration at which an effect is observed; Table 6) and NOEC (Highest concentration at with no effect is observed; Table 6) were also observed. The products of diazinon hydrolysis by OpdA were confirmed by mass spectroscopy to be diethyl thiophosphoric acid and 2-isopropyl-4 methyl-pyrimidin-6-ol, consistent with the characterised mechanism of phosphotriesterases. These data demonstrate that OpdA performed in a predictable manner and that its action significantly detoxified the phosphotriester insecticide. As the skilled person will appreciate, considering the relationship between A900 and OpdA, A900 will work in a similar manner.

TABLE 6

Toxicity of diazinon to Ceriodaphnia dubia before and after treatment with OpdA.

| | Untreated diazinon | | OpdA treated diazinon* | | Fold improved survival | |
|---|---|---|---|---|---|---|
| | 24 hours | 48 hours | 24 hours | 48 hours | 24 hours | 48 hours |
| EC 50 (μg/L)** | 0.389 | 0.195 | 73,000 | 46,100 | $1.9 \times 10^5$ | $1.9 \times 10^5$ |
| LOEC (μg/L)** | 0.55 | 0.275 | 100,000 | 100,000 | | |
| NOEC (μg/L)** | 0.275 | 0.138 | 30,000 | 30,000 | | |

*OpdA dosed at a rate of 0.05 g/L. The values shown are the mean of two replicates that differed by less than 10% at each reading.
**EC50, effective concentration for 50% survival; LOEC, Lowest concentration at which an effect is observed; NOEC: Highest concentration at which no effect is observed.

Extensive ecotoxicological data are also available for another OP insecticide, chlorpyriphos, and its hydrolysis products (diethyl thiophosphoric acid and TCP; 3,5,6 trichloropyridin-2-ol) (Barron and Woodburn, 1995). Both products are considerably less toxic than the parent compound in indicator species such as Bluegill (*Lepomis macrochirus*) (Mayer and Ellersieck, 1986) and TCP has also been shown to be of low to moderate toxicity to aquatic and terrestrial biota (Barron ad Woodburn, 1995). Hydrolysis of insecticidal phosphotriesters by enzymes of the invention therefore represents a significant reduction in their mammalian toxicities and ecotoxicities.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/509,810 filed 20 Jul. 2011, and U.S. 61/510,377 filed 21 Jul. 2011; of which the entire contents of both are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Afriat et al. (2006) Biochemistry 45: 13677-13686.
Barron and Woodburn (1995) In Reviews of Environmental Contamination and
Toxicology, Springer-Verlag: New York, 144: 1-93.
Broomfield et al. (1999) Chemico-Biological Interactions 119-120: 413-418.
Buchbinder et al. (1998) Biochemistry 37: 5096-5160.
Cadwell and Joyce (1992) PCR Methods Appl. 2:28-33.
Campbell et al. (1998) Insect Biochem. Mol. Biol. 28: 139-150.
Capecchi (1980) Cell 22:479-488.
Cheng et al. (1999) Chemico-Biological Interactions 119-120: 455-462.
Cho et al. (2004) Appl. Environ. Microbiol. 70:4681-4685.
Clapp (1993) Clin. Perinatol. 20:155-168.
Coco et al. (2001) Nature Biotechnology 19:354-359.
Coco et al. (2002) Nature Biotechnology 20:1246-1250.
Crameri et al. (1998) Nature 391:288-291.
Curiel et al. (1992) Hum. Gen. Ther. 3:147-154.
Davies et al. (1997) FEBS Letters 410: 378-382.
Dong et al (2005) Journal of Molecular Biology 353: 655-663
Dumas et al. (1989a) Biotechnology and Applied Biochemistry 11: 235-243.
Dumas et al. (1989b) Journal of Biological Chemistry 264: 19659-19665.
Dumas et al. (1990) Experientia 46: 729-731.
Eggert et al. (2005) Chembiochem 6:1062-1067.
Eglitis et al. (1988) Biotechniques 6:608-614.
Fujimura et al. (1985) Plant Tissue Culture Letters 2:74.
Gan et al. (1991) Drug Metabolism and Disposition 19: 100-106.
Gordon et al. (1999) Chemical-Biological Interactions 14:463-470.
Graham et al. (1973) Virology 54:536-539.
Harper et al. (1988) Appl. Environ. Microbiol. 54: 2586-2589.
Hellinga (1997) Proc. Natl. Acad. Sci. 94:10015-10017.
Horne et al. (2002) Appl. Environ. Microbiol. 68: 3371-3376.
Horne et al. (2006) FEMS Microbiology Letters 259:187-194.
Jackson et al. (2006) Biochem. J. 397:501-508.
Jackson et al. (2009) Appl Environ Microbiol. 75:5153-5156.
Jézéquel et al. (2008) Biotechniques 45:523-532.
Koziel et al. (1996) Plant Mol Biol 32:393-405.
LeJuene et al. (1998) Nature 395:27-28.
Leung et al. (1989) Technique 1:11-15.
Lu et al. (1993) J. Exp. Med. 178:2089-2096.
Mayer and Ellersieck (1986) Manual of Acute Toxicity: Interpretation and Database for 410 Chemicals and 66 Species of Freshwater Animals. U.S. Department of Interior: Washington, D.C.
Mulbry (1992) Gene 121: 149-153.
Mulbry and Karns (1989) Journal of Bacteriology 171: 6740-6746.
Mulbry and Kearney (1991) Crop Protection 10: 334-345.
Needleman and Wunsch (1970) J. Mol. Biol. 48:443-453.
Ness et al. (2002) Nature Biotechnology 20:1251-1255.
Ostermeier et al. (1999) Nature Biotechnology 17:1205-1209.
Petrikovics et al. (2000a) Toxicology Science 57: 16-21.
Petrikovics et al. (2000b) Drug Delivery 7: 83-89.
Rekha et al. (2000) Critical Reviews in Biotechnology 20: 213-235.
Russell et al. (2001) Aust. Biotechnol. 11: 24-26.
Scanlan and Reid (1995) Chemistry and Biology 2: 71-75.
Sieber et al. (2001) Nature Biotechnology 19:456-460.
Stemmer (1994a) Proc. Natl. Acad. Sci. USA 91:10747-10751.
Stemmer (1994b) Nature 370:389-391.
Toriyama et al. (1986) Theor. Appl. Genet. 205:34.
Volkov et al. (1999) Nucleic acids research 27(18):e18.
Wagner et al. (1992) Proc. Natl. Acad. Sci. USA 89:6099-6103.
Wang et al. (1993) J Biochem Toxicol 8: 161-166.
Wang et al. (1998) J Biochem Mol Toxicol 12: 213-217.
Wu et al. (2000) J Am Chem Soc 122:10206-10207.
Yang et al. (2003) Protein Eng. 16:135-145.
Zhao et al. (1998) Nature Biotechnology 16:258-261.

The invention claimed is:

1. A polypeptide comprising:
   i) the amino acid sequence as set forth in SEQ ID NO:1, or
   ii) an amino acid sequence which is at least 95% sequence identical to i) comprising:
      a) a valine at a position corresponding to amino acid number 51 of SEQ ID NO:1,
      b) an alanine at a position corresponding to amino acid number 63 of SEQ ID NO:1,
      c) an arginine at a position corresponding to amino acid number 156 of SEQ ID NO:1,
      d) a glutamic acid at a position corresponding to amino acid number 203 of SEQ ID NO:1, and
      e) an aspartic acid at a position corresponding to amino acid number 236 of SEQ ID NO:1,
   wherein the polypeptide has organophosphate hydrolysing activity.

2. The polypeptide of claim 1, wherein the polypeptide has greater organophosphate hydrolysing activity than a second polypeptide comprising the sequence of amino acids set forth in SEQ ID NO:2, SEQ ID NO:3 or SEQ ID NO:4.

3. The polypeptide of claim 1 which has two or more of:
   i) at least a 2 fold higher second order rate constant ($k_{cat}/K_m$) for chlorpyrifos methyl than a polypeptide comprising the sequence of amino acids set forth in SEQ ID NO:2, SEQ ID NO:3, or SEQ ID NO:4,
   ii) at least a 1.5 fold higher second order rate constant ($k_{cat}/K_m$) for diazinon than a polypeptide comprising the sequence of amino acids set forth in SEQ ID NO:2, SEQ ID NO:3, or SEQ ID NO:4,
   iii) at least a 2 fold higher second order rate constant ($k_{cat}/K_m$) for parathion ethyl than a polypeptide comprising the sequence of amino acids set forth in SEQ ID NO:2, SEQ ID NO:3, or SEQ ID NO:4, or
   iv) at least a 1.2 fold higher catalytic constant ($k_{cat}$) for chlorpyrifos ethyl than a polypeptide comprising the sequence of amino acids set forth in SEQ ID NO:2, SEQ ID NO:3, or SEQ ID NO:4.

4. The polypeptide of claim 1, wherein a leaving group of the organophosphate has a pKa of less than 8, and/or the organophosphate is an aromatic non-vinyl organophosphate.

5. The polypeptide of claim 1 which has two or more of:
   i) a second order rate constant ($k_{cat}/K_m$) for chlorpyrifos ethyl of at least about $2 \times 10^6$ sec$^{-1} \cdot$M$^{-1}$,
   ii) a $k_{cat}/K_m$ for chlorpyrifos methyl of at least about $3.5 \times 10^5$ sec$^{-1} \cdot$M$^{-1}$,
   iii) a $k_{cat}/K_m$ for diazinon of at least about $3.6 \times 10^6$ sec$^{-1} \cdot$M$^{-1}$,
   iv) a $k_{cat}/K_m$, for parathion ethyl of at least about $9 \times 10^7$ sec$^{-1} \cdot$M$^{-1}$, or
   v) a $k_{cat}/K_m$ for parathion methyl of at least about $3 \times 10^6$ sec$^{-1} \cdot$M$^{-1}$.

6. The polypeptide of claim 1 which is a fusion protein further comprising at least one other polypeptide sequence.

7. The polypeptide of claim 1 which is immobilized on a solid support.

8. An extract of a host cell comprising the polypeptide of claim 1.

9. A composition comprising a polypeptide of claim 1, and one or more acceptable carriers.

10. A method for hydrolysing an organophosphate molecule(s), the method comprising contacting the organophosphate molecule(s) with a polypeptide of claim 1.

11. A biosensor for detecting the presence of an organophosphate, the biosensor comprising a polypeptide of claim 1, and a means for detecting hydrolysis of an organophosphate molecule by the polypeptide.

12. A composition comprising an extract of claim 8, and one or more acceptable carriers.

13. A method for hydrolysing an organophosphate molecule(s), the method comprising contacting the organophosphate(s) molecule with an extract of claim 8.

14. The polypeptide of claim 1, comprising an amino acid sequence which is at least 99% sequence identical to the amino acid sequence set forth in SEQ ID NO: 1.

* * * * *